(12) United States Patent
Yatabe

(10) Patent No.: US 10,576,188 B2
(45) Date of Patent: Mar. 3, 2020

(54) COATING AGENT AND MEDICAL INSTRUMENT SURFACE TREATED WITH COATING AGENT

(71) Applicant: TERUMO KABUSHIKI KAISHA, Shibuya-ku, Tokyo (JP)

(72) Inventor: Teruyuki Yatabe, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 43 days.

(21) Appl. No.: 15/855,255

(22) Filed: Dec. 27, 2017

(65) Prior Publication Data
US 2018/0117220 A1    May 3, 2018

Related U.S. Application Data

(63) Continuation of application No. PCT/JP2016/067591, filed on Jun. 13, 2016.

(30) Foreign Application Priority Data

Jul. 1, 2015    (JP) .................. 2015-132846

(51) Int. Cl.

| A61L 31/10 | (2006.01) |
|---|---|
| C09D 183/04 | (2006.01) |
| C09D 183/08 | (2006.01) |
| A61M 5/32 | (2006.01) |
| A61L 31/00 | (2006.01) |
| C08G 77/26 | (2006.01) |
| C08G 77/54 | (2006.01) |
| C08G 77/04 | (2006.01) |

(52) U.S. Cl.
CPC .............. *A61L 31/10* (2013.01); *A61L 31/00* (2013.01); *A61M 5/32* (2013.01); *A61M 5/329* (2013.01); *C09D 183/04* (2013.01); *C09D 183/08* (2013.01); *A61L 2420/02* (2013.01); *A61L 2420/06* (2013.01); *A61M 2205/0222* (2013.01); *A61M 2207/00* (2013.01); *C08G 77/04* (2013.01); *C08G 77/26* (2013.01); *C08G 77/54* (2013.01)

(58) Field of Classification Search
CPC ... A61L 31/10; A61L 2420/02; C09D 183/08; A61M 5/32; A61M 5/329; C08G 77/16; C08K 5/544; C08K 5/5435; C08L 83/06
See application file for complete search history.

(56) References Cited

U.S. PATENT DOCUMENTS

| 6,015,398 A | 1/2000 | Arimatsu et al. |
| 2001/0021832 A1* | 9/2001 | Numao .................. A61L 31/10 |
| | | 604/272 |

FOREIGN PATENT DOCUMENTS

| JP | 7-178159 A | 7/1995 |
| JP | 2001-190654 A | 7/2001 |
| JP | 2008-260840 A | 10/2008 |
| JP | 2013-112686 A | 6/2013 |

OTHER PUBLICATIONS

International Search Report (PCT/ISA/210) dated Sep. 27, 2016, by the Japanese Patent Office as the International Searching Authority for International Application No. PCT/JP2016/067591.
Written Opinion (PCT/ISA/237) dated Sep. 27, 2016, by the Japanese Patent Office as the International Searching Authority for International Application No. PCT/JP2016/067591.
English translation of Written Opinion (PCT/ISA/237) dated Sep. 27, 2016, by the Japanese Patent Office as the International Searching Authority for International Application No. PCT/JP2016/067591.
European Search Report dated Jul. 12, 2018 for European Application No. 16817709.5-1107 (6 pages).
XP-002786666, Database WPI, Week 199537, Thomson Scientific, London, GB,; AN 1995-279970 & JPH07178159 A (Terumo Corp) Jul. 18, 1995.

* cited by examiner

*Primary Examiner* — Kuo Liang Peng
(74) *Attorney, Agent, or Firm* — Buchanan, Ingersoll & Rooney PC

(57) ABSTRACT

A coating agent that has excellent durability and a medical instrument (for example, a needle) that has been coated with the coating agent, are provided. The coating agent includes a condensate (1) of a compound represented by the following general formula (1-1) with a compound represented by the following general formula (1-2),

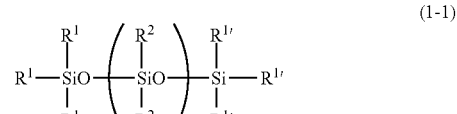

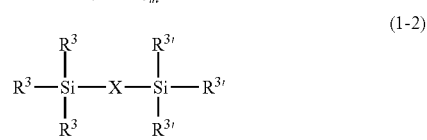

a polydiorganosiloxane (2), and an amino-group-containing polyorganosiloxane (3). The content ratio of the polydiorganosiloxane (2) is 30 to 75 mass %, based on the total mass of the condensate (1), the polydiorganosiloxane (2), and the amino-group-containing polyorganosiloxane (3).

18 Claims, 3 Drawing Sheets

COATING AGENT AND MEDICAL INSTRUMENT SURFACE TREATED WITH COATING AGENT

CROSS-REFERENCES TO RELATED APPLICATIONS

This application is a continuation of International Application No. PCT/JP2016/067591 filed on Jun. 13, 2016, and claims priority to Japanese Application No. 2015-132846 filed on Jul. 1, 2015, the entire content of which is incorporated herein by reference.

TECHNICAL FIELD

The disclosure generally relates to a coating agent and a medical instrument surface treated with the coating agent.

BACKGROUND DISCUSSION

At present, not only patients suffering from diseases but also healthy persons undergo various medical practices such as medical examinations. For example, injections are used for the patients suffering from diseases, for the purpose of injecting a liquid medicine for therapy, anesthesia at the time of surgery, or the like. In addition, even healthy persons often undergo injections such as blood donation and preventive inoculation. However, injections exert considerable burden on patients and healthy persons, due to a pain at the time of puncture, discomfort at the time of injection of a liquid medicine, or the like. In view of this, for the purpose of alleviating the pain, a variety of investigations have been made on the shape of tip portions of injection needles, coating agents for injection needle surfaces, and the like. Among these, as a coating agent for injection needle surfaces, silicones have been mainly used. The silicone coating agents impart a lubricating property to the injection needle, thereby reducing friction at the time of puncture. Therefore, an injection needle coated with a silicone coating agent alleviates the pain at the time of injection. For example, Japanese Patent Laid-open No. 1995-178159 discloses a silicone coating agent that contains an amino-group-containing polyorganosiloxane and a polydiorganosiloxane in a specific mixing ratio. An injection needle coated with this coating agent exhibits excellent piercing characteristics.

SUMMARY

However, even with the injection needle coated with the coating agent described in Japanese Patent Laid-open No. 1995-178159, it is impossible not to give any pain to the subject such as a patient. Accordingly, further enhancement of piercing characteristics can be desirable.

In addition, a needle coated with the silicone coating agent may be used for puncturing multiple times. For example, a needle having been subjected to a silicone coating treatment may be used in injecting a liquid medicine to a patient, after being made to pierce a stopper of a medicine bottle for sucking the liquid medicine. For example, a reservoir needle having been subjected to a silicone coating treatment may be made to re-puncture a different infusion bag, in the situation of infusion bag replacement. In such cases, there can be a problem that the coating agent may peel off the needle surface, increasing the friction (puncture resistance) during use and giving a pain to the patient. For this reason, further enhancement of durability (a restraining or preventing effect on exfoliation of the coating) can be desirable.

Accordingly, aspects of the present disclosure have been made in consideration of the aforesaid circumstances. According to an exemplary aspect, provided is a coating agent excellent in durability and a medical instrument (for example, a needle) surface treated (coated) with the coating agent.

According to an exemplary aspect, provided is a coating agent enhanced in piercing characteristics and a medical instrument (for example, a needle) surface treated (coated) with the coating agent.

According to an exemplary aspect, for example, it is possible to address the aforesaid problem by using a coating agent that contains an alkoxysilane having at least —NR— (where R is each independently a hydrogen atom or a monovalent hydrocarbon group) and a hydroxyl group, in addition to a polydiorganosiloxane and an amino-group-containing polyorganosiloxane, and that contains the aforesaid polydiorganosiloxane in a specified amount.

According to an exemplary aspect, provided is a coating agent including (a) a condensate (1) of a compound represented by the following general formula (1-1):

[Chemical 1]

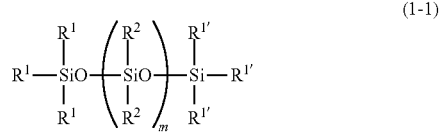

wherein each $R^1$ and each $R^{1'}$ independently represents a monovalent hydrocarbon group or a hydroxyl group (—OH), provided that at least one of $R^1$ and at least one of $R^{1'}$ is the hydroxyl group (—OH), each $R^2$ independently represents a monovalent hydrocarbon group, and m is an integer of 1,000 to 30,000, with a compound represented by the following general formula (1-2):

[Chemical 2]

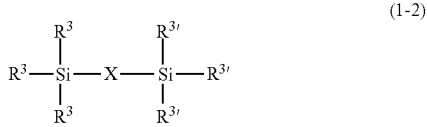

wherein each $R^3$ and each $R^{3'}$ independently represents a $C_1$-$C_4$ monovalent hydrocarbon group or a $C_1$-$C_4$ alkoxy group, provided that at least one of $R^3$ and at least one of $R^{3'}$ is the $C_1$-$C_4$ alkoxy group, X is a divalent group having at least one —NR— (wherein each R is independently a hydrogen atom or a monovalent hydrocarbon group) and at least one hydroxyl group (—OH);

(b) a polydiorganosiloxane represented by the following general formula (2):

[Chemical 3]

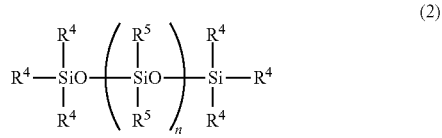

(2)

wherein each $R^4$ and $R^5$ each independently represents a monovalent hydrocarbon group, and n is an integer of 8 to 1,000; and (c) an amino-group-containing polyorganosiloxane containing at least one amino group in one molecule thereof represented by the following general formula (3):

[Chemical 4]

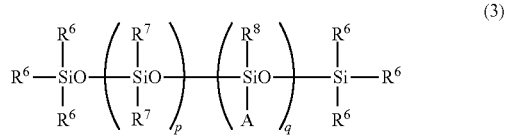

(3)

wherein each $R^6$ independently represents a monovalent hydrocarbon group or a $-OR^9$ group, wherein each $R^9$ independently represents a substituted or unsubstituted $C_1$-$C_4$ monovalent hydrocarbon group, each $R^7$ and each $R^8$ independently represents a monovalent hydrocarbon group, each A independently represents an amino-group-containing group, p:q=(5 to 100):1 (that is, a ratio of p:q is in a range of from 5:1 to 100:1), and q is an integer of 1 to 100, in which the content ratio of the polydiorganosiloxane (2) is 30 to 75 mass %, based on the total mass of the condensate (1), the polydiorganosiloxane (2) and the amino-group-containing polyorganosiloxane (3).

DETAILED DESCRIPTION

Figure 1A:
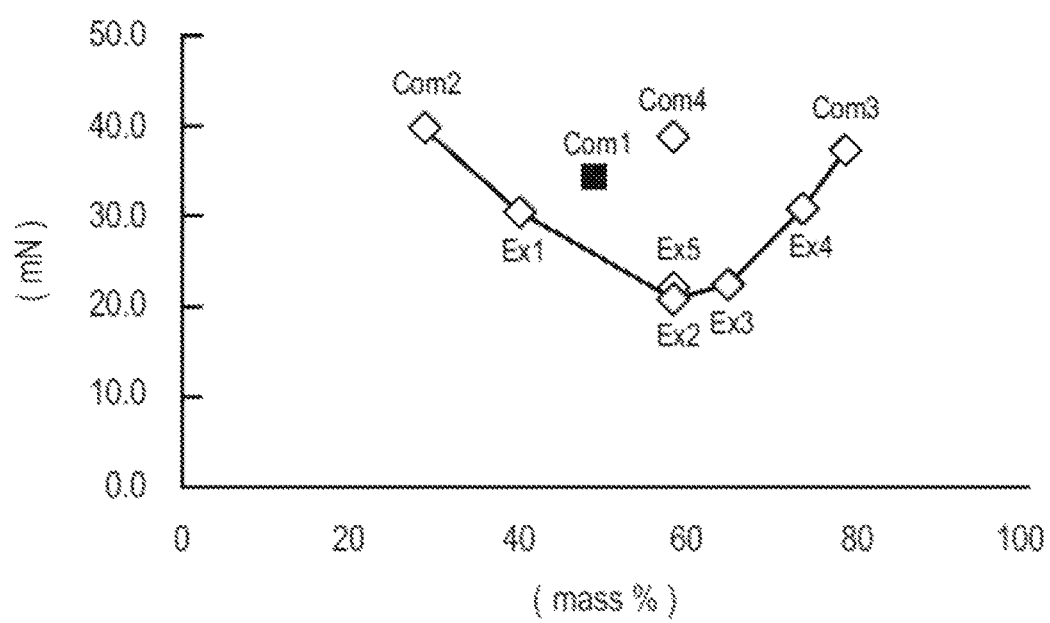
FIG. 1A is a graph depicting puncture resistance (sliding resistance value (mN)) at an initial stage (on puncturing zero time) of a needle surface treated with a coating agent by heating, in Examples 1 to 5 (Ex. 1 to Ex. 5) and Comparative Examples 1 to 4 (Com. 1 to Com. 4).

An exemplary coating agent includes:

(a) a condensate (1) of a compound represented by the following general formula (1-1):

[Chemical 5]

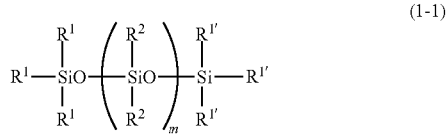

(1-1)

where $R^1$ and $R^{1'}$ each independently represent a monovalent hydrocarbon group or a hydroxyl group (—OH), provided that at least one of $R^1$ and at least one of $R^{1'}$ are hydroxyl groups (—OH), $R^2$ each independently represents a monovalent hydrocarbon group, and m is an integer of 1,000 to 30,000, with a compound represented by the following general formula (1-2):

[Chemical 6]

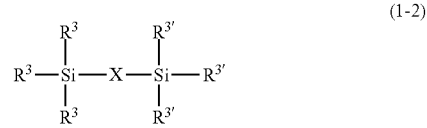

(1-2)

where $R^3$ and $R^{3'}$ each independently represent a $C_1$-$C_4$ monovalent hydrocarbon group or a $C_1$-$C_4$ alkoxy group, provided that at least one of $R^3$ and at least one of $R^{3'}$ are alkoxy groups, and X is a divalent group having at least one —NR— (where R is each independently a hydrogen atom or a monovalent hydrocarbon group) and at least one hydroxyl group (—OH);

(b) a polydiorganosiloxane (2) represented by the following general formula (2):

[Chemical 7]

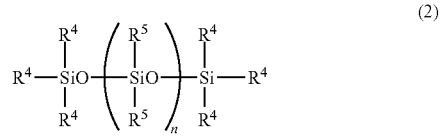

(2)

where $R^4$ and $R^5$ each independently represent a monovalent hydrocarbon group, and n is an integer of 8 to 1,000; and (c) an amino-group-containing polyorganosiloxane containing at least one amino group in one molecule thereof represented by the following general formula (3):

[Chemical 8]

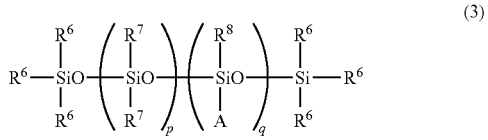

(3)

where $R^6$ each independently represents a monovalent hydrocarbon group or a —$OR^9$ group, provided that $R^9$ each independently represents a substituted or unsubstituted $C_1$-$C_4$ monovalent hydrocarbon group, $R^7$ and $R^8$ each independently represent a monovalent hydrocarbon group, A each independently represents an amino-group-containing group, p:q=(5 to 100):1 (that is, a ratio of p:q is in a range of from 5:1 to 100:1), and q is an integer of 1 to 100, in which the content ratio of the polydiorganosiloxane (2) is 30 to 75 mass %, based on the total mass of the condensate (1), the polydiorganosiloxane (2) and the amino-group-containing polyorganosiloxane (3).

According to an exemplary embodiment, a coating agent having the aforesaid configuration forms a firm coating film, and is excellent in adhesion to a surface of a substrate (for example, a medical instrument such as a needle, a catheter, a cannula, etc.), so that exfoliation of the coating from the substrate can be restrained or prevented and excellent durability is ensured. In addition, the coating agent according to an exemplary embodiment is excellent in lubricating property. Therefore, a needle surface treated with the coating agent according to an exemplary embodiment can be reduced in friction (puncture resistance) at the time of puncturing, and can be enhanced in piercing characteristics.

Note that herein the compound represented by the general formula (1-1) is referred to as the "compound (1-1)," the compound represented by the general formula (1-2) is referred to as the "compound (1-2)," the condensate of the compound (1-1) with the compound (1-2) is referred to as the "condensate (1)," the polydiorganosiloxane represented by the general formula (2) is referred to as the "polydiorganosiloxane (2)," and the amino-group-containing polyorganosiloxane containing at least one amino group in one molecule thereof represented by the general formula (3) is referred to as the "amino-group-containing polyorganosiloxane (3)."

According to an exemplary embodiment, the coating agent includes the condensate (1), the polydiorganosiloxane (2) and the amino-group-containing polyorganosiloxane (3). According to an exemplary embodiment, the coating agent contains the polydiorganosiloxane (2) in an amount of 30 to 75 mass % (provided that the total amount of the condensate (1), the polydiorganosiloxane (2) and the amino-group-containing polyorganosiloxane (3) is 100 mass %). According to an exemplary embodiment, the coating agent can reduce friction, and is excellent in piercing characteristics. In addition, the coating agent, for example, is excellent in adhesion to a surface of a substrate (for example, a needle, a catheter, a cannula, a three-way cock), and, therefore, exfoliation of a surface treatment product (coating film) obtained by the coating agent from the substrate can be restrained or prevented, and excellent durability is ensured. Note that the present disclosure is not limited by the following discussion concerning the reason why the aforesaid exemplary effects can be achieved.

Without being bound by any particular theory, extensive and intensive investigations on further enhancement of adhesion to substrate, durability and puncture characteristics of coating agents were conducted. For example, according to an exemplary aspect, for enhancing the durability, it can be effective to increase the number of crosslinking points where molecules of an amino-group-containing polyorganosiloxane can react (bind) or where an amino-group-containing polyorganosiloxane and a polyorganosiloxane can react (bind).

For example, certain coating agents can include an amino-group-containing polyorganosiloxane having an amino group at a terminal or in a constitutional unit thereof and a polydiorganosiloxane (one terminated with a triorganosilyl group). For example, the polydiorganosiloxane, by its organosiloxane moiety, imparts a lubricating property to a coating film (enhances piercing characteristics). For example, of the amino-group-containing polyorganosiloxane, the polyorganosiloxane moiety imparts a lubricating property, and the amino group binds to the substrate (for example, hydroxyl groups at a surface of a metallic substrate) to form a coating film. Therefore, the amino-group-containing polyorganosiloxane contributes to lubricating property, adhesion to substrate, and film forming properties. However, although the amino-group-containing polyorganosiloxane has a property for binding to the substrate, there is no crosslinking point where molecules of the amino-group-containing polyorganosiloxane can react (bind) or where the amino-group-containing polyorganosiloxane and a polyorganosiloxane can react (bind).

As a result of extensive and intensive investigation of a method for increasing the number of such crosslinking points according to an exemplary aspect disclosed herein, means by which adhesion to substrate and durability can be further enhanced by further enhancing network-forming property on a substrate of a coating film formed by use of the aforesaid coating agent has been discovered. Specifically, it has been discovered that according to an exemplary aspect disclosed herein, adhesion and durability of the coating agent can be further enhanced when the coating agent includes the condensate (1), the polydiorganosiloxane (2) and the amino-group-containing polyorganosiloxane (3) and the content ratio of the polydiorganosiloxane (2) is set at a specified value.

For example, the condensate (1) has —NR— and a hydroxyl group (—OH) in its structure. These groups interact with a substrate surface, for example, with hydroxyl groups in the substrate surface, so that adhesion to the substrate is excellent. For example, in the coating agent, the amino-group-containing polyorganosiloxane (3) can also be bound with the substrate through the amino group. Therefore, for example, a coating film formed by use of the coating agent is higher in adhesion to the substrate, exfoliation of the coating film from the substrate can be restrained or prevented more effectively, and durability can be enhanced, as compared to the case where the coating agents described in Japanese Patent Laid-open No. 1995-178159 are used.

For example, the condensate (1) is a product of condensation between the hydroxyl group (the substituent group $R^1$ or $R^{1'}$) present in the compound (1-1) and the alkoxy group (the substituent group $R^3$ or $R^{3'}$) present in the compound (1-2). For example, the compound (1-2) has the crosslinking points for condensation with the compound (1-1), the number of the crosslinking points being as large as at most six per one compound of the general formula (1-2). Therefore, the condensate (1) can be bound with a large number of hydroxyl groups derived from the compound (1-1), through the crosslinking points (the alkoxy groups as the substituent groups $R^3$ or $R^{3'}$) of the compound (1-2). In addition, the condensate (1) can be condensed also with hydroxyl groups derived from the compound (1-1) of other condensates (1), through the crosslinking points (the alkoxy groups as the substituent groups $R^3$ or $R^{3'}$) of the compound (1-2). Therefore, for example, when the coating agent is used, a network which is three-dimensional broader and stronger can be formed. For this reason, for example, the coating film formed by use of the coating agent is a more rigid film, and durability can be enhanced, as compared to the case where the coating agents described in Japanese Patent Laid-open No. 1995-178159 are used.

Therefore, a medical instrument (for example, a medical instrument on which friction is generated at the time of insertion into a living body, such as a needle, a catheter, a cannula, or a three-way cock) surface treated with an exemplary coating agent can restrain or prevent exfoliation of the surface treatment product (coating film) obtained by the coating agent from the substrate, and can maintain a lubricating property for a long time (is excellent in durability). In addition, an exemplary coating agent can reduce friction with the substrate, and is excellent in piercing characteristics. Therefore, for example, when a needle surface treated with an exemplary coating agent is used, exfoliation of the coating film (coating agent) from the needle surface is prevented or restrained even in the case where the needle is used multiple times. For this reason, a high lubricating property can be maintained, and therefore friction (puncture resistance) during use can be reduced, so that a pain given to the patient can be alleviated effectively. Further, the use of an exemplary coating agent makes it possible to restrain or prevent the coating film from being exfoliated from the needle (substrate) surface. Accordingly, even when the needle surface treated with an exemplary coating agent is made to re-puncture an infusion bag, mixing of foreign matter (peeled matter of coating film) into the infusion bag is restrained or prevented, which can be desirable from the viewpoint of safety.

For example, an exemplary coating agent contains the polydiorganosiloxane (2) in an amount of 30 to 75 mass % (provided that the total amount of the condensate (1), the polydiorganosiloxane (2) and the amino-group-containing polyorganosiloxane (3) is 100 mass %). While the polydiorganosiloxane (2) contributes to lubricating property as aforementioned, when it is used in the aforesaid content ratio, it can exhibit a good lubricating property and can, therefore, reduce friction (puncture resistance) during use. For example, if the aforesaid content ratio is less than 30 mass %, a sufficient lubricating property cannot be obtained, and friction (puncture resistance) becomes large. On the other hand, for example, if the aforesaid content ratio exceeds 75 mass %, the content ratios of the other components (the condensate (1) and the amino-group-containing polyorganosiloxane (3)) become low, so that it becomes difficult to form a firm network, and the coating film becomes liable to peel off the substrate. Consequently, it becomes impossible to obtain a sufficient durability.

For example, the amino-group-containing polyorganosiloxane (3) and the organosiloxane moiety of the polydiorganosiloxane (2) impart a lubricating property, and on the other hand, the organosiloxane moiety of the condensate (1) can also impart a lubricating property. Therefore, a coating film formed by use of an exemplary coating agent is enhanced in lubricating property and can reduce friction (puncture resistance). For this reason, when a needle surface treated with an exemplary coating agent is used, the pain which the puncture gives to the patient can be further alleviated.

For example, when an exemplary coating agent is applied to a substrate, durability and lubricating property (piercing characteristics) can be enhanced. In addition, when an exemplary coating agent is applied to a substrate, a good balance of lubricating property, adhesion and coating film-forming property can be achieved. Therefore, an exemplary coating agent can be particularly suitably used for medical instruments where it is desirable to have the aforesaid characteristics, for example, needles such as injection needles. According to an exemplary aspect, provided is a medical instrument (for example, a medical instrument on which friction is generated at the time of insertion into a living body, such as a needle, a catheter, or a cannula) surface treated with a coating agent. Such a medical instrument can ensure that exfoliation of the coating film (coating agent) from the medical instrument surface is prevented or restrained even in the case where the medical instrument is used multiple times. For this reason, a high lubricating property can be maintained, and therefore friction (puncture resistance) during use can be reduced, so that the pain given to the patient can be alleviated effectively. Furthermore, the use of an exemplary coating agent makes it possible to restrain or prevent the coating film from peeling off the medical instrument (substrate) surface. Therefore, even when a needle surface treated with an exemplary coating agent is made to re-puncture an infusion bag, mixing of foreign matter (peeled matter of coating film) into the infusion bag is restrained or prevented, which can be desirable from the viewpoint of safety. In addition, for example, while a three-way cock is not inserted into a living body, a sliding property of an operating part of the three-way cock can be maintained.

Exemplary embodiments will be described below. Herein, "X to Y" indicating a range includes X and Y, and means "not less than X and not more than Y." In addition, unless specified otherwise, operations and measurement of physical properties and the like are conducted under the conditions of room temperature (20° C. to 25° C.) and a relative humidity of 40 to 50% RH.

Note that while an exemplary embodiment in which the medical instrument is a needle will be described in detail below, the present disclosure is not limited to this specific embodiment. For example, the present disclosure is similarly applicable to other medical instruments such as a catheter.

[Condensate (1)]

The condensate (1) according to an exemplary aspect is a condensate of a compound (1-1) represented by the following general formula (1-1):

[Chemical 9]

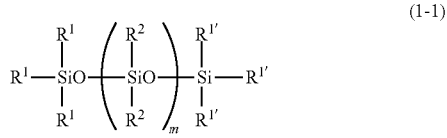
(1-1)

with a compound (1-2) represented by the following general formula (1-2):

[Chemical 10]

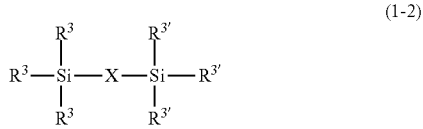
(1-2)

The condensate (1) according to an exemplary aspect has —NR— and a hydroxyl group (—OH). These groups interact with a substrate, for example, hydroxyl groups of a substrate, and, therefore, are excellent in adhering property for adhesion to the substrate. For this reason, these groups promote adhesion to the substrate, together with the amino group present in the amino-group-containing polyorganosiloxane (3). In addition, for example, the condensate (1) is a product of condensation between the hydroxyl group (substituent groups $R^1$ and $R^{1'}$) present in the compound (1-1) and the alkoxy group (substituent groups $R^3$ and $R^{3'}$) present in the compound (1-2). For example, the compound (1-2) has crosslinking points for condensation with the compound (1-1), the number of the crosslinking points being as large as at most six per one compound of the general formula (1-2). Therefore, for example, the condensate (1) can be bound with a large number of hydroxyl groups derived from the compound (1-1) through the crosslinking point (the alkoxy group as the substituent group $R^3$ or $R^{3'}$) of the compound (1-2). In addition, for example, the condensate (1) is condensed also with hydroxyl groups derived from the compound (1-1) of other condensates (1) through the crosslinking points of the compound (1-2). In addition, for example, the condensate (1) is condensed also with $R^6$ (for example, —$OR^9$ group) in the compound (3) through the crosslinking point (the alkoxy group as the substituent group $R^3$ or $R^{3'}$) of the compound (1-2). Therefore, for example, when the coating agent is used, it is possible to form a network which is three-dimensionally broader and firmer. Accordingly, for example, a coating film formed by use of the coating agent is firm, so that durability can be enhanced. For this reason, for example, when a needle surface treated with the coating agent is used, exfoliation of the coating film (coating agent) from the needle surface is prevented or restrained, even in the case where the needle is made to puncture a rubber stopper a plurality of times. Therefore, for example, the needle surface treated with the coating agent can maintain a high lubricating property, so that friction (puncture resistance) during use is small, and the pain given to the patient can be reduced effectively. For example, even when a needle surface treated with the coating agent is made to re-puncture an infusion bag, peeling of the coating film (coating agent) from the needle surface and mixing of the foreign matter (peeled matter of coating film) into the infusion bag can be restrained or prevented, which can be desirable from the viewpoint of safety. In addition, for example, since the aforesaid condensate (1) has an organosiloxane moiety (—$Si(R^2)_2O$—), it can impart a lubricating property (ease of piercing). For example, the coating agent may include a single kind of condensate (1) or may include two or more kinds of condensates (1).

In addition, for example, the condensate (1) is a condensate of the compound (1-1) with the compound (1-2). The structure of the condensate (1) formed from condensation of the compound (1-1) with the compound (1-2) is not particularly limited. For example, the structure can be, for example, a form of a mixture. For example, the condensation takes place by a reaction between the hydroxyl group (the substituent group $R^1$, $R^{1'}$) present in the compound (1-1) and the alkoxy group (the substituent group $R^3$, $R^{3'}$) present in the compound (1-2).

The foregoing is exemplified below. For example, description is made by taking a case in which the compound (1-2) to be detailed below is a compound which is represented by the general structure (1-2), in which the two $R^3$ groups are methoxy groups (alkoxy groups), and the remaining $R^3$ group is a methyl group (hydrocarbon group), and the three $R^{3'}$ groups are methoxy groups (alkoxy groups), namely, which is represented by the following structure:

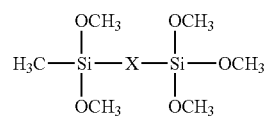

as an example.

For example, the condensate (1) of the compound (1-1) with the compound (1-2) can include one or more of the following structures represented by [Chemical 12], [Chemical 13], [Chemical 14], [Chemical 15], [Chemical 16], and [Chemical 17]:

[Chemical 12]

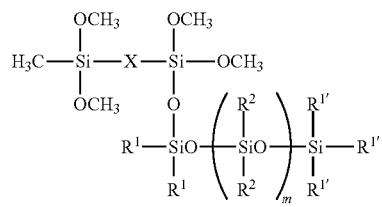

which is obtained by a reaction between one of the methoxy groups (alkoxy groups) as $R^{3'}$ present in the compound (1-2) and the hydroxyl group of one of $R^1$ and $R^{1'}$ present in the compound (1-1);

[Chemical 13]

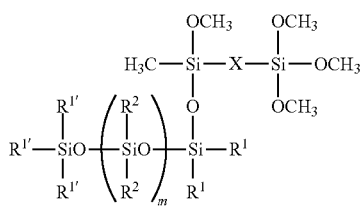

which is obtained by a reaction between one of the methoxy groups (alkoxy groups) as $R^3$ present in the compound (1-2) and the hydroxyl group of one of $R^1$ and $R^{1'}$ present in the compound (1-1);

[Chemical 14]

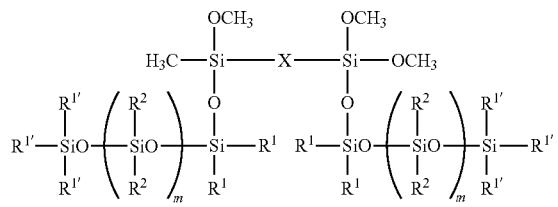

which is obtained by a reaction of one of the methoxy groups (alkoxy groups) as $R^3$ and one of the methoxy groups (alkoxy groups) as $R^{3'}$ present in the compound (1-2) with the hydroxyl group of one of $R^1$ and $R^{1'}$ present in the compound (1-1);

[Chemical 15]

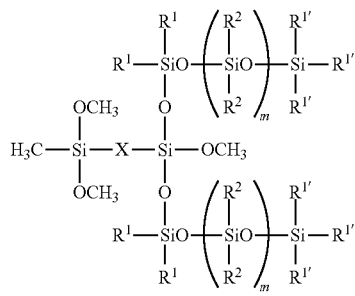

which is obtained by a reaction between two of the methoxy groups (alkoxy groups) as $R^{3'}$ present in the compound (1-2) and the hydroxyl group of one of $R^1$ and $R^{1'}$ present in the compound (1-1);

[Chemical 16]

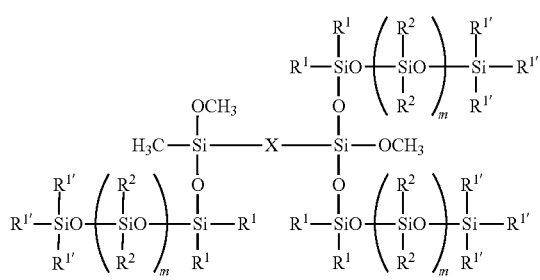

which is obtained by a reaction of one of the methoxy groups (alkoxy groups) as $R^3$ and two of the methoxy groups (alkoxy groups) as $R^{3'}$ present in the compound (1-2) with the hydroxyl group of one of $R^1$ and $R^{1'}$ present in the compound (1-1);

[Chemical 17]

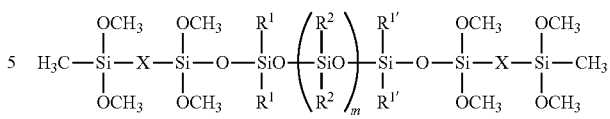

which is obtained by a reaction between one of the methoxy groups (alkoxy groups) as $R^{3'}$ present in the compound (1-2) and the hydroxyl groups present at both terminals of the compound (1-1).

For example, the condensate (1) of the compound (1-1) with the compound (1-2) can include compounds in which a plurality of the aforesaid condensations are generated, and combinations of two or more of the aforesaid. Note that the aforesaid forms of condensation are examples, and are not restrictive. For example, the compound (1-1) and the compound (1-2) react with each other through hydrolysis, to form a network on a three-dimensional basis. Therefore, for example, the presence of the condensate (1) makes it possible to form a firm coating film and to significantly enhance durability.

For example, the compound (1-1) is represented by the following general formula (1-1):

[Chemical 18]

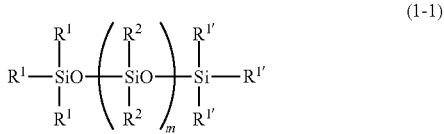

(1-1)

Note that in the case where a plurality of constitutional units represented by the formula: $-Si(R^2)_2O-$ are present, the constitutional units may be identical or may be different. In addition, the compound (1) may be prepared by use of a single kind of compound (1-1) or may be prepared by use of two or more kinds of compounds (1-1).

In the aforesaid general formula (1-1), $R^1$ and $R^{1'}$ represent a monovalent hydrocarbon group or a hydroxyl group (—OH). For example, $R^1$ and $R^{1'}$ may be identical or different. In $-Si(R^1)_3$, the plurality of $R^1$ groups may be identical or different. Similarly, in $-Si(R^{1'})_3$, the plurality of $R^{1'}$ groups may be identical or different. For example, that at least one of $R^1$ groups and at least one of $R^{1'}$ groups are hydroxyl groups (—OH). Taking into account an effect of enhancing a coating film-forming property and the like, for example, one or two of $R^1$ groups and/or one or two of $R^{1'}$ groups are hydroxyl groups. For example, one of $R^1$ groups and one of $R^1$ groups are hydroxyl groups.

In the aforesaid general formula (1-1), the monovalent hydrocarbon groups as $R^1$ and $R^{1'}$ are not particularly limited, and example thereof include $C_1$-$C_{24}$ straight-chain or branched alkyl groups, $C_2$-$C_{24}$ straight-chain or branched alkenyl groups, $C_3$-$C_9$ cycloalkyl groups, and $C_6$-$C_{30}$ aryl groups. For example, the $C_1$-$C_{24}$ straight-chain or branched alkyl groups are not specifically restricted, and examples thereof include methyl, ethyl, n-propyl, isopropyl, n-butyl, isobutyl, sec-butyl, tert-butyl, n-pentyl, isopentyl, tert-pentyl, neopentyl, 1,2-dimethylpropyl, n-hexyl, isohexyl, 1,3-dimethylbutyl, 1-isopropylpropyl, 1,2-dimethylbutyl, n-heptyl, 1,4-dimethylpentyl, 3-ethylpentyl, 2-methyl-1-isopropylpropyl, 1-ethyl-3-methylbutyl, n-octyl, 2-ethylhexyl, 3-methyl-1-isopropylbutyl, 2-methyl-1-isopropyl, 1-t-butyl-2-methylpropyl, n-nonyl, 3,5,5-trimethylhexyl, n-decyl, isodecyl, n-undecyl, 1-methyldecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, n-docosyl, n-tricosyl, and n-tetracosyl. The $C_2$-$C_{24}$ straight-chain or branched alkenyl groups are not particularly limited, and examples thereof include vinyl, 1-propenyl, 2-propenyl (allyl), isopropenyl, 1-butenyl, 2-butenyl, 3-butenyl, 1-pentenyl, 2-pentenyl, 3-pentenyl, 1-hexenyl, 2-hexenyl, 3-hexenyl, 1-heptenyl, 2-heptenyl, 5-heptenyl, 1-octenyl, 3-octenyl, 5-octenyl, dodecenyl, and octadecenyl. The $C_3$-$C_9$ cycloalkyl groups are not specifically restricted, and examples thereof include cyclopropyl, cyclobutyl, cyclopentyl, cyclohexyl, cycloheptyl, and cyclooctyl. The $C_6$-$C_{30}$ aryl groups are not particularly limited, and examples thereof include phenyl, biphenyl, terphenyl, pentalenyl, indenyl, naphthyl, azlenyl, heptalenyl, biphenylenyl, fluorenyl, acenaphthylenyl, pleiadenyl, acenaphthenyl, phenalenyl, phenanthryl, anthryl, fluoranthenyl, acephenanthrylenyl, aceanthrylenyl, triphenylenyl, pyrenyl, crysenyl, and naphthacenyl.

Among these, from the viewpoint of an effect of enhancing lubricating property and durability and compatibility with solvents, the monovalent hydrocarbon groups as $R^1$ and $R^{1'}$ can be $C_1$-$C_{16}$ straight-chain or branched alkyl groups, for example, $C_1$-$C_8$ straight-chain or branched alkyl groups, for example, $C_1$-$C_4$ straight-chain or branched alkyl groups, for example, methyl groups. Note that the aforesaid "compatibility" refers to mutual solubility between different kinds of molecules, and means ease of mixing at a molecular level.

In the aforesaid general formula (1-1), $R^2$ represents a monovalent hydrocarbon group. For example, the $R^2$ groups present in one constituent unit may be identical or different. In addition, in the case where a plurality of constituent units are present, the constituent units may be identical or different. The monovalent hydrocarbon group as $R^2$ can be selected from the examples set forth for the aforesaid $R^1$ and $R^{1'}$, and, therefore, description thereof is omitted here. From the viewpoint of an effect of enhancing lubricating property and durability and compatibility with solvents, $R^2$ is, for example, a $C_1$-$C_{16}$ straight-chain or branched alkyl group, for example, a $C_1$-$C_8$ straight-chain or branched alkyl group, for example, a $C_1$-$C_4$ straight-chain or branched alkyl group, for example, a methyl group.

An exemplary embodiment is such that in the general formula (1-1), one of $R^1$ groups and one of $R^{1'}$ groups are hydroxyl groups, the rest of the $R^1$ and $R^{1'}$ groups are each independently a $C_1$-$C_4$ straight-chain or branched alkyl group, and $R^2$ is each independently a $C_1$-$C_4$ straight-chain or branched alkyl group. An exemplary embodiment lies in that in the general formula (1-1), one of $R^1$ groups and one of $R^{1'}$ groups are hydroxyl groups, and the rest of the $R^1$ and $R^{1'}$ groups and $R^2$ are methyl groups.

In addition, m is an integer of 1,000 to 30,000, for example, 5,000 to 20,000, for example, an integer of more than 10,000 and not more than 18,000, for example, an integer of more than 10,000 and not more than 15,000. When m is in the aforesaid range, the compound (1-1), and, further, the condensate (1) having a moiety derived from the compound (1-1), has a sufficient amount of an organosiloxane moiety and, therefore, can exhibit a sufficient lubricating property to further reduce friction (puncture resistance). While the molecular weight of the compound (1-1) is not particularly limited, its weight average molecular weight can be 10,000 to 2,000,000, for example, 100,000 to 1,050,000, for example, 100,000 to 1,000,000, for example, 500,000 to 1,000,000. Herein the weight average molecular weight means a value determined by a calibration curve method from measurement results obtained by gel permeation chromatography (GPC) with polystyrene as a standard substance. Note that the structure of the compound (1-1) can be easily confirmed from the structure of the condensate (1). Therefore, the weight average molecular weight of the compound (1-1) can be determined based on the structure of the condensate (1) (particularly a moiety corresponding to the compound (1-1)).

The compound (1-2) is represented by the following general formula (1-2):

[Chemical 19]

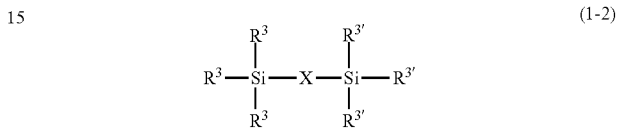

(1-2)

The condensate (1) may be prepared by use of a single kind of compound (1-2) or may be prepared by use of two or more kinds of compounds (1-2).

In addition, in the aforesaid general formula (1-2), $R^3$ and $R^{3'}$ represent a $C_1$-$C_4$ monovalent hydrocarbon group or a $C_1$-$C_4$ alkoxy group. For example, $R^3$ and $R^{3'}$ groups may be identical or different. In —$Si(R^3)_3$, the plurality of $R^3$ groups may be identical or different. Similarly, in —$Si(R^{3'})_3$, the plurality of $R^{3'}$ groups may be identical or different. For example, at least one of $R^3$ groups and at least one of $R^{3'}$ groups are alkoxy groups. For example, two or three of $R^3$ groups and/or two or three of $R^{3'}$ groups are alkoxy groups. For example, all three of $R^3$ groups and all three of $R^{3'}$ groups are alkoxy groups.

In the case where the condensate (1) includes a plurality of compounds (1-2) of the aforesaid general formula (1-2), the compounds (1-2) may be identical or different and, for example, can be identical.

In the aforesaid general formula (1-2), the $C_1$-$C_4$ monovalent hydrocarbon groups as $R^3$ and $R^{3'}$ are not particularly limited, and examples thereof include methyl, ethyl, propyl, isopropyl, butyl, isobutyl, sec-butyl, and tert-butyl. From the viewpoint of condensability with the compound (1-1) or the like, the monovalent hydrocarbon groups can be $C_1$-$C_4$ alkyl groups, for example, methyl or ethyl groups, for example, methyl groups. In addition, the $C_1$-$C_4$ alkoxy groups are not specifically restricted, and examples thereof include methoxy, ethoxy, propoxy, isopropoxy, butoxy, sec-butoxy, and tert-butoxy. From the viewpoint of condensability with the compound (1-1) or the like, the $C_1$-$C_4$ alkoxy groups can be $C_1$-$C_4$ alkoxy groups, for example, methoxy or ethoxy groups, for example, methoxy groups.

In addition, in the aforesaid general formula (1-2), X has at least one —NR— (where R is independently a hydrogen atom or a monovalent hydrocarbon group) and at least one hydroxyl group (—OH). For example, in the case where X has two or more —NR— groups, the substituent groups R may be identical or different.

While X in the compound (1-2) contains —NR— and hydroxyl group, it is exemplary from the viewpoint of enhancing adhesion and durability that either one of the —NR— group and the hydroxyl group is contained in the number of two or more in X. In other words, it is exemplary that the total number of these groups is three or more. On the other hand, there is no particularly upper limit for the total number of these groups, but, taking into account the lubricating property of the coating agent and the availability of the compound and the like factors, the total number can be not more than five.

With the number of these substituent groups increased, more firm binding to a substrate surface can be achieved, so that adhesion and durability are further enhanced.

The monovalent hydrocarbon group as R in the aforesaid —NR— group can be selected from the examples set forth for the aforesaid $R^1$ and $R^{1'}$, and, therefore, description thereof is omitted here. From the viewpoint of an effect of enhancing condensability, adhesion and durability and the like factors, R can be a hydrogen atom or a $C_1$-$C_8$ straight-chain or branched alkyl group, for example, a hydrogen atom or a $C_1$-$C_4$ straight-chain or branched alkyl group, for example, a hydrogen atom.

X in the compound (1-2) may have other groups (constituent moieties) so long as it has the aforesaid substituent group —NR— and hydroxyl group. Such groups (constituent moieties) are not particularly limited, and examples thereof include —O— (oxygen atom), —S— (sulfur atom), and divalent hydrocarbon groups. The aforesaid divalent hydrocarbon groups are not specifically restricted, and examples thereof include $C_1$-$C_{24}$ straight-chain or branched alkylene groups, and $C_6$-$C_{24}$ arylene groups. Such groups (constituent moieties) may be used either singly or in combination of two or more of them.

The $C_1$-$C_{24}$ straight-chain or branched alkylene groups are not particularly limited, and examples thereof include methylene, ethylene, trimethylene, propylene, tetramethylene, 2-methyltrimethylene, 1-methyltrimethylene, 1-ethylethylene, 1,2-dimethylethylene, 1,1-dimethylethylene, pentamethylene, 1-propylethylene, 1-isopropylethylene, hexamethylene, 1-butylethylene, 1-isobutylethylene, 1,1-dimethylethylene, trimethylhexamethylene, octamethylene, and decamethylene.

The $C_6$-$C_{24}$ arylene groups are not specifically restricted, and examples thereof include phenylene, naphthylene, anthracenylene, phenanthrenylene, pyrenylene, perylenylene, fluorenylene, and biphenylene.

From the viewpoint of an effect of enhancing condensability, adhesion and durability and the like factors, the other groups (constituent moieties) contained in X can be —O— (oxygen atom) and $C_1$-$C_{24}$ straight-chain or branched alkylene groups, for example, —O— (oxygen atom) and $C_1$-$C_6$ straight-chain or branched alkylene groups, for example, —O— (oxygen atom) and $C_1$-$C_3$ straight-chain or branched alkylene groups, for example, ethylene and trimethylene groups.

Further, from the viewpoint of an effect of enhancing condensability, adhesion and durability and the like factors, X in the compound (1-2) can be a divalent group represented by the following general formula (i):

[Chemical 20]

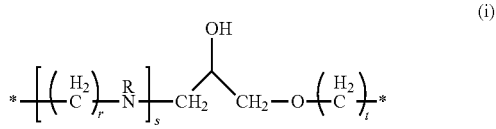

where R is each independently a hydrogen atom or a monovalent hydrocarbon group, r, s and t are each independently an integer of 1 to 6, and

* represents a binding position. In the case where two or more constituent units represented by the formula: —($CH_2$)$_r$—(NR)— are present (s is not less than two), the constituent units may be identical or different.

The aforesaid R can be selected from the examples set forth for R of —NR-contained in X of the compound (1-2), and, therefore, description thereof is omitted here. From the viewpoint of an effect of enhancing condensability, adhesion and durability and the like factors, R can be a hydrogen atom or a $C_1$-$C_8$ straight-chain or branched alkyl group, for example, a hydrogen atom or a $C_1$-$C_4$ straight-chain or branched alkyl group, for example, a hydrogen atom.

In the aforesaid general formula (i), r represents the number of methylene groups, and, from the viewpoint of an effect of enhancing lubricating property and durability, compatibility with solvents, and the like factors, r can be an integer of 1 to 4, for example, an integer of 2 to 3. In addition, s represents the number of constituent units represented by the formula: —($CH_2$)$_r$—(NR)—, and, from the viewpoint of an effect of enhancing lubricating property and durability, compatibility with solvents, and the like factors, s can be an integer of 2 to 4, for example, an integer of 2 to 3. Further, t represents the number of methylene groups, and, from the viewpoint of an effect of enhancing lubricating property and durability, compatibility with solvents, and the like factors, t can be an integer of 1 to 4, for example, an integer of 2 to 3. Therefore, an exemplary embodiment is such that in the general formula (i), r is an integer of 2 to 3, s is an integer of 2 to 3, and t is an integer of 2 to 3.

In the aforesaid general formula (i), symbols * each represent a binding position for binding to —Si($R^3$)$_3$ and —Si($R^{3'}$)$_3$ in the aforesaid general formula (1-2). Note that the symbols * at both terminals represented by the general formula (i) can bind to either of —Si($R^3$)$_3$ and —Si($R^{3'}$)$_3$. For example, a configuration in which in the case where the symbol * at the left-side terminal of the general formula (i) binds to —Si($R^{3'}$)$_3$, the symbol * at the right-side terminal binds to —Si($R^3$)$_3$ may be used, or a reverse configuration may be used.

Examples of the compound (1-2) containing X represented by the aforesaid general formula (i) include, but are not limited to, the following compounds (A) to (L).

[Chemical 21]

[Compound (A)]

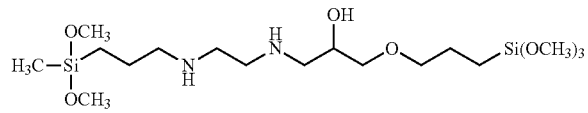

[Compound (B)]

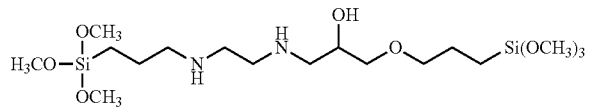

[Compound (C)]
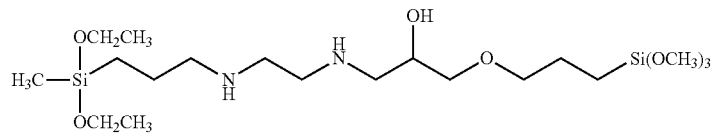

[Compound (D)]
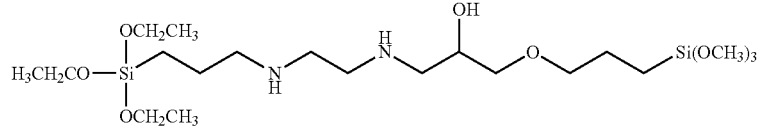

[Chemical 22]

[Compound (E)] [Compound (F)]
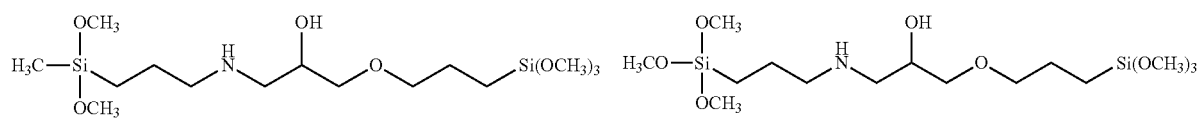

[Compound (G)] [Compound (H)]
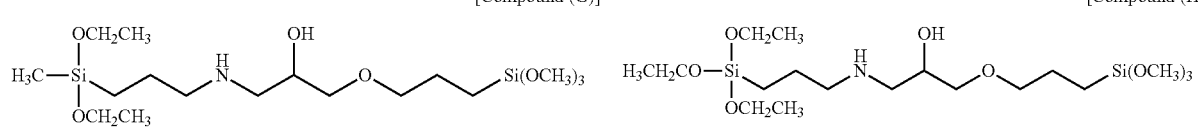

[Chemical 23]

[Compound (I)]

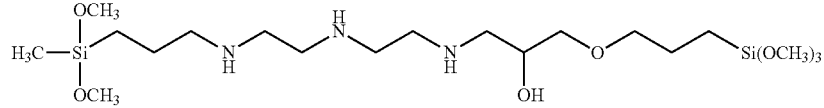

[Compound (J)]
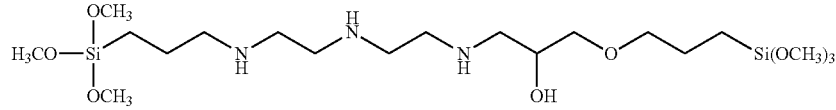

[Compound (K)]
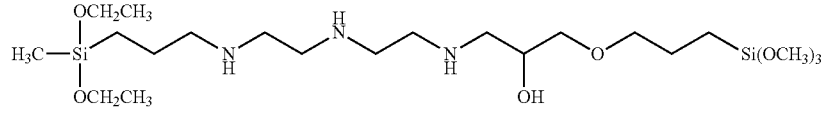

[Compound (L)]
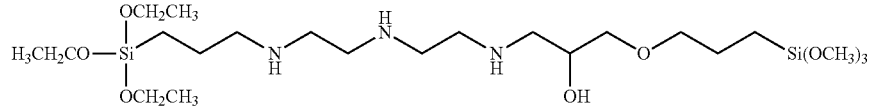

The compounds (A) to (L) can be used, for example, as the compound (1-2). The condensate (1) obtained by use of such a compound (1-2) interacts firmly with a substrate (is excellent in adhesion), and has a multiplicity of crosslinking points, so that it can form a firm film. Therefore, a coating film formed by use of the coating agent containing the aforesaid condensate (1) can impart excellent piercing characteristics (lubricating property) and durability.

As the aforesaid compound (1-2), commercialized ones may be used, or ones obtained by synthesis may be used. The method for synthesizing the aforesaid compound (1-2) is not particularly limited; for example, the compound (1-2) can be obtained by a condensation reaction between an alkoxysilane having an amino group and an alkoxysilane having a glycidyl group. The reaction conditions when performing the reaction are also not particularly limited, and the same or similar conditions to any suitable condensation conditions or appropriately modified conditions can be adopted.

For example, the condensate (1) is obtained by condensation of the compound (1-1) with the compound (1-2). The method for condensation of the compound (1-1) with the compound (1-2) is not specifically restricted, and any suitable condensation methods can be applied in the same manner or through appropriate modification. For example, a method of reacting the compound (1-1) with the compound (1-2) in an appropriate solvent, optionally in the presence of a catalyst, is exemplary. For example, the appropriate solvent is not particularly limited, and a solvent can be used which can dissolve the aforesaid compounds (1-1) and (1-2) and which is low in reactivity with the compounds (1-1) and (1-2). For example, an organic solvent having no active proton can be used, and benzene, toluene, xylene, cumene, dioxane, tetrahydrofuran, hexane, pentane, heptane and the like can be used. The aforesaid solvents may be used either singly or in the form of a mixed liquid of two or more of them. The aforesaid solvent can be preliminarily subjected to a dehydration treatment. For example, the amount of the solvent to be used is not particularly limited, and can be an amount wherein the total concentration of the compounds (1-1) and (1-2) is approximately 5 to 30 mass %.

For example, in the aforesaid method, the mixing ratio of the compounds (1-1) and (1-2) is not particularly limited so long as it is such a ratio that the condensation of the compound (1-1) with the compound (1-2) can proceed. For example, the amount of the compound (1-2) can be 1 to 50 parts by mass, for example, 3 to 30 parts by mass, per 100 parts by mass of the compound (1-1). When such amounts are adopted, the compound (1-1) and the compound (1-2) can be efficiently condensed. The condensation conditions for the compound (1-1) and the compound (1-2) are also not particularly limited so long as they are such ratios that the condensation of the compound (1-1) and the compound (1-2) can proceed. For example, the condensation temperature can be 50° C. to 100° C., for example, 70° C. to 90° C. In addition, the condensation time can be 7 to 20 hours, for example, 8 to 16 hours. Under such conditions, the condensation of the compound (1-1) with the compound (1-2) proceeds efficiently, and the desired condensate (1) can be prepared in high yield.

Note that as aforementioned, the condensation of the compound (1-1) with the compound (1-2) may be conducted in the presence of an appropriate catalyst. The catalyst which can be used in this case is not specifically restricted, and any suitable catalyst can be used. Specific examples of the usable catalyst include platinum complexes such as chloroplatinic acid, platinum-olefin complex, platinum-vinylsiloxane complex, etc., platinum catalysts having platinum black or platinum supported on a carrier, rhodium catalysts such as chlorotris(triphenylphosphine)rhodium, etc., nickel catalysts such as dichlorobis(triphenylphosphine)nickel, etc., and cobalt catalysts such as dicobalt octacarbonyl.

The molecular weight of the condensate (1) obtained by the condensation of the compound (1-1) with the compound (1-2) is not particularly limited, and the weight average molecular weight can be 10,000 to 2,000,000, for example, 100,000 to 1,050,000, for example, 100,000 to 1,000,000, for example, 500,000 to 1,000,000.

In addition, the reaction product obtained by the aforesaid condensation reaction may, if desired, further be purified by any suitable means such as silica gel column chromatography. Note that the aforesaid condensate (1) may be mixed with an amino-group-containing polyorganosiloxane (3) and a polydiorganosiloxane (2) after preliminarily prepared, or may be mixed with an amino-group-containing polyorganosiloxane (3) and a polydiorganosiloxane (2) while performing the condensation reaction.

In an exemplary coating agent, the content ratio of the condensate (1) is not particularly limited so long as it can satisfy the content ratio of the polydiorganosiloxane (2) aforesaid, and it can be 2.3 to 8.0 mass %, based on the total mass of the condensate (1), the polydiorganosiloxane (2) and the amino-group-containing polyorganosiloxane (3). In the case where two or more kinds of condensates (1) are contained, the total mass of them can be in the aforesaid range.

With the content ratio of the condensate (1) set within the aforesaid range, for example, easy formation of a firm network is ensured, a coating film-forming property is enhanced, and the strength of the coating film formed can be enhanced. As a result, durability of the coating film can be further enhanced. For example, with the content ratio of the condensate (1) set within the aforesaid range, adhesion to a substrate and lubricating property (ease of piercing, or a piercing resistance-reducing effect) can be enhanced more effectively. In addition, safety of the coating agent can be further enhanced, which can be desirable in the case of application to medical uses, such as a needle. From such a viewpoint, the condensate (1) can be contained in an amount of 3.0 to 7.5 mass %, for example, 3.3 to 5.5 mass %, for example, 3.3 to 4.5 mass %, based on the total amount of the condensate (1), the polydiorganosiloxane (2) and the amino-group-containing polyorganosiloxane (3).

The condensate (1) can be mixed with the amino-group-containing polyorganosiloxane (3) in an appropriate ratio. For example, the condensate (1) can be contained in a ratio of more than 1 part by mass and not more than 50 parts by mass, for example, 5 to 20 parts by mass, for example, 6 to 15 parts by mass, for example, 8.0 to 10.7 parts by mass, based on 100 parts by mass of the amino-group-containing polyorganosiloxane (3). When such a mixing ratio of the condensate (1) and the amino-group-containing polyorganosiloxane (3) is used, for example, the effect by the condensate (1) and the amino-group-containing polyorganosiloxane (3) is exhibited more remarkably, a firmer coating film can be formed, and lubricating property (ease of piercing, or a piercing resistance-reducing effect) can be further enhanced.

[Polydiorganosiloxane (2)]

The polydiorganosiloxane (2) according to an exemplary aspect is represented by the following general formula (2):

[Chemical 24]

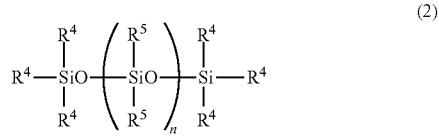

(2)

As represented by the aforesaid structure, the polydiorganosiloxane (2) is a polydiorganosiloxane which has a triorganosilyl group at molecular chain terminals and does not contain an amino group in its molecule, and substantially contains no hydroxyl group and no hydrolysable group in its molecule.

The polydiorganosiloxane (2), by its organosiloxane moiety, imparts a lubricating property to a coating film formed by the condensate (1) and the amino-group-containing polyorganosiloxane (3). Due to the presence of the polydiorganosiloxane (2), therefore, the coating film formed can exhibit a high lubricating property (ease of piercing, or piercing resistance-reducing effect). In the case where a plurality of constituent units represented by the formula: —Si($R^5$)$_2$O— are present, the constituent units may be identical or different. Further, the coating agent may contain a single kind of polydiorganosiloxane (2), or may contain two or more kinds of polydiorganosiloxanes (2).

In the aforesaid general formula (2), $R^4$ and $R^5$ represent monovalent hydrocarbon groups. For example, the plurality of $R^4$ groups may be identical or different. Similarly, the plurality of $R^5$ groups may be identical or different. The monovalent hydrocarbon groups as $R^4$ can be selected from the examples set forth for $R^1$ and $R^{1'}$ in the aforesaid general formula (1-1), and, therefore, description thereof is omitted here. The monovalent hydrocarbon groups as $R^5$ can be selected from the examples set forth for $R^2$ in the aforesaid general formula (1-1), and, therefore, description thereof is omitted here. Among these, the monovalent hydrocarbon groups as $R^4$ and $R^5$ can be $C_1$-$C_{16}$ straight-chain or branched alkyl groups, for example, $C_1$-$C_8$ straight-chain or branched alkyl groups, for example, $C_1$-$C_4$ straight-chain or branched alkyl groups, for example, methyl groups, from the viewpoint of a further enhancing effect on lubricating property and the like factors.

In the aforesaid general formula (2), n is an integer of 8 to 1,000, for example, an integer of 10 to 200, for example, an integer of 10 to 100, for example, an integer of not less than 20 and less than 90, for example, an integer of 25 to 70, for example, an integer of 30 to 50, for example, an integer of not less than 30 and less than 50. With n in such a range, the polydiorganosiloxane (2) exhibits a sufficient lubricating property, whereby friction with a substrate (puncture resistance) can be further reduced. Therefore, the molecular weight of the polydiorganosiloxane (2) is not particularly limited, and the weight average molecular weight can be 500 to 7,000, for example, 1,500 to 5,000, for example, 2,000 to 4,000.

Examples of the polydiorganosiloxane (2) include polydimethylsiloxane, polydiethylsiloxane, polydipropylsiloxane, polydiisopropylsiloxane, polymethylethylsiloxane, polymethylpropylsiloxane, polymethylisopropylsiloxane polyethylpropylsiloxane, and polyethylisopropylsiloxane. Among these, polydimethylsiloxane is exemplary, from the viewpoint of lubricating property (piercing characteristics) and the like.

As the aforesaid polydiorganosiloxane (2), commercialized ones may be used, or ones obtained by synthesis may be used.

In the coating agent according to an exemplary aspect, the content ratio of the polydiorganosiloxane (2) is 30 to 75 mass %, based on the total mass of the condensate (1), the polydiorganosiloxane (2) and the amino-group-containing polyorganosiloxane (3). In the case where two or more kinds of polydiorganosiloxanes (2) are contained, the total mass of them is within the aforesaid range.

For example, if the amount of the polydiorganosiloxane (2) is less than 30 mass %, lubricating property (ease of piercing, or a piercing resistance-reducing effect) is poor, which may be undesirable. In contrast, if the amount of the polydiorganosiloxane (2) exceeds 75 mass %, the contents of the other indispensable ingredients, namely, the condensate (1) and the amino-group-containing polyorganosiloxane (3), may be too low, so that the effect by these ingredients cannot be exhibited sufficiently. The polydiorganosiloxane (2) can be contained in an amount of 35 to 75 mass %, for example, 40 to 70 mass %, for example, 45 to 70 mass %, for example, 50 to 65 mass %, based on the total amount of the condensate (1), the polydiorganosiloxane (2) and the amino-group-containing polyorganosiloxane (3). With the polydiorganosiloxane (2) used in such an amount, lubricating property (ease of piercing, or a piercing resistance-reducing effect) can be enhanced further effectively.

[Amino-Group-Containing Polyorganosiloxane (3)]

The amino-group-containing polyorganosiloxane (3) according to an exemplary aspect is represented by the following general formula (3):

[Chemical 25]

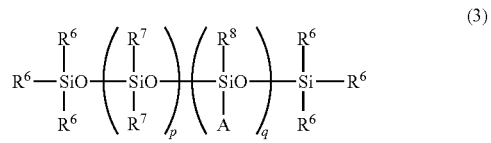

The amino-group-containing polyorganosiloxane (3) can bind (adhere) to a substrate by interacting with hydroxyl groups present in the substrate, for example, at the substrate surface through the amino group (the substituent group "A" in the general formula (3)). In addition, the organosiloxane moiety (—Si($R^7$)$_2$O—) present in the amino-group-containing polyorganosiloxane (3) imparts lubricating property (ease of piercing). Note that in the case where two or more constituent units of the formula: —Si($R^7$)$_2$O— are present (p is not less than two), the constituent units may be identical or different. Similarly, in the case where two or more constituent units of the formula: —Si($R^8$)(A)O— are present (q is not less than 2), the constituent units may be identical or different. Further, the coating agent may contain a single kind of amino-group-containing polyorganosiloxane (3), or may contain two or more kinds of amino-group-containing polyorganosiloxanes (3).

In the aforesaid general formula (3), $R^6$ is a monovalent hydrocarbon group or a —$OR^9$ group. For example, the plurality of $R^6$ groups may be identical or different. The monovalent hydrocarbon group as $R^6$ can be selected from the examples set forth for $R^1$ and $R^{1'}$ in the aforesaid general formula (1-1), and, therefore, description thereof is omitted here. For example, $R^6$ can be $C_1$-$C_{16}$ straight-chain or branched alkyl groups, for example, $C_1$-$C_8$ straight-chain or branched alkyl groups, for example, $C_1$-$C_4$ straight-chain or branched alkyl groups, for example, methyl groups, from the viewpoint of an effect of further enhancing lubricating property, compatibility with solvents, and the like factors.

In addition, $R^9$ each independently represents a substituted or unsubstituted $C_1$-$C_4$ monovalent hydrocarbon group. For example, in the case where the plurality of $R^1$ groups are —$OR^9$ groups, the plurality of —$OR^9$ groups may be identical or different from one another. For example, the monovalent hydrocarbon group is not specifically restricted, and can be, for example, a $C_1$-$C_4$ straight-chain or branched alkyl group (methyl, ethyl, n-propyl, isopropyl, n-butyl, isobutyl, sec-butyl, tert-butyl), a $C_2$-$C_4$ straight-chain or branched alkenyl group (vinyl, 1-propenyl, 2-propenyl (allyl), isopropenyl, 1-butenyl, 2-butenyl, 3-butenyl), or a $C_3$ or $C_4$ cycloalkyl group (cyclopropyl, cyclobutyl). Among these, methyl and ethyl groups are exemplary from the viewpoint of an effect of further enhancing lubricating property, adhesion to a substrate, and the like factors.

In the aforesaid general formula (3), $R^7$ and $R^8$ each independently represent a monovalent hydrocarbon group. For example, the plurality of $R^7$ groups may be identical or different. Similarly, the plurality of $R^8$ groups may also be identical or different. For example, the monovalent hydrocarbon group as $R^7$ and $R^8$ is not particularly limited, and can be selected from the examples set forth for the monovalent hydrocarbon group as the aforesaid substituent group "$R^6$." Among these, exemplary are $C_1$-$C_4$ straight-chain alkyl groups, for example, a methyl group, from the viewpoint of an effect of further enhancing lubricating property, availability, and the like factors.

In the aforesaid general formula (3), A represents an amino-group-containing group. For example, in the case where a plurality of A groups are present (q is not less than two), the A groups may be identical or different. The amino-group-containing group is not particularly limited, and examples thereof include β-aminoethyl, γ-aminopropyl, N-(β-aminoethyl)aminomethyl, and γ-(N-(β-aminoethyl) amino)propyl. Among these, examples include γ-aminopropyl, N-(β-aminoethyl)aminomethyl or γ-(N-(β-aminoethyl) amino)propyl, for example, γ-(N-(β-aminoethyl)amino) propyl or γ-aminopropyl, for example, γ-(N-(β-aminoethyl) amino)propyl, from the viewpoint of an effect of further enhancing lubricating property, adhesion to a substrate, and the like factors.

From the foregoing, an exemplary embodiment is such that in the general formula (3), $R^6$ is each independently a $C_1$-$C_4$ straight-chain or branched alkyl group, $R^7$ and $R^8$ groups are each independently a $C_1$-$C_4$ straight-chain or branched alkyl group, and A is γ-aminopropyl, N-(β-aminoethyl)aminomethyl or γ-(N-(β-aminoethyl)amino)propyl group. An exemplary embodiment is such that in the general formula (3), $R^6$ is methyl, $R^7$ and $R^8$ are methyl, and A is γ-(N-(β-aminoethyl)amino)propyl.

In addition, in the aforesaid general formula (3), q is an integer of 1 to 100, for example, an integer of 3 to 20, for example, an integer of 3 to 15, for example, an integer of 4 to 10. For example, q is an integer which together with p satisfies the relation of p:q=(5 to 100):1 (molar ratio). For example, p and q can satisfy the following: p:q=(10 to 100):1, for example, (20 to 80):1, for example, (30 to 50):1. That is, a ratio of p:q is in a range of from 5:1 to 100:1, for example, from 20:1 to 80:1, for example, from 30:1 to 50:1. With p and q being as aforesaid, for example, a sufficient number of amino groups are present in the amino-group-containing polyorganosiloxane (3), and, therefore, sufficient adhesion to a substrate can be achieved. For example, with such p and q, a sufficient number of organosiloxane moieties are present in the amino-group-containing polyorganosiloxane (3), so that the coating agent can exhibit a sufficient lubricating property, thereby further reducing friction with a substrate (puncture resistance). While p is not particularly limited so long as it satisfies the aforesaid relation, p can be 10 to 800, for example, 60 to 400, for example, 100 to 300.

The molecular weight of the amino-group-containing polyorganosiloxane (3) is not particularly limited, but the weight average molecular weight can be 5,000 to 50,000, for example, 7,500 to 30,000, for example, 10,000 to 20,000.

In an exemplary coating agent, the content ratio of the amino-group-containing polyorganosiloxane (3) is not particularly limited so long as it can satisfy the content ratio of the polydiorganosiloxane (2) aforesaid, and it can be 20 to 62 mass % based on the total mass of the condensate (1), the polydiorganosiloxane (2) and the amino-group-containing polyorganosiloxane (3). In the case where two or more kinds of amino-group-containing polyorganosiloxanes (3) are contained, it is exemplary that the total mass of these is within the aforesaid range.

With the content ratio of the amino-group-containing polyorganosiloxane (3) set to be not less than 20 mass %, adhesion to a substrate can be enhanced, and exfoliation of the coating agent can be restrained. In addition, with the content ratio of the amino-group-containing polyorganosiloxane (3) set to be not more than 62 mass %, the content ratios of the other indispensable ingredients, namely, the condensate (1) and the polydiorganosiloxane (2), can be sufficiently secured, so that the effect of these ingredients can be sufficiently exhibited.

Further, it is exemplary that the amino-group-containing polyorganosiloxane (3) is contained in an amount of 24 to 55 mass %, for example, in an amount of 30 to 50 mass %, for example, in an amount of 30 to 40 mass %, based on the total amount of the condensate (1), the polydiorganosiloxane (2) and the amino-group-containing polyorganosiloxane (3). With such an amount, adhesion to a substrate and lubricating property (ease of piercing, or a piercing resistance-reducing effect) can be enhanced effectively. In addition, safety of the coating agent can be further enhanced, which can be desirable in the case of application to medical uses, such as a needle.

A method of preparing the amino-group-containing polyorganosiloxane (3) according to an exemplary aspect is not specifically restricted. For instance, the amino-group-containing polyorganosiloxane (3) can be prepared in the same manner as, or with appropriate modification of, the method described in, for example, Japanese Patent Laid-open No. 1995-178159.

An exemplary coating agent contains the condensate (1), the polydiorganosiloxane (2) and the amino-group-containing polyorganosiloxane (3). The coating agent may be composed only of the condensate (1), the polydiorganosiloxane (2) and the amino-group-containing polyorganosiloxane (3), or may further contain other ingredients in addition to the aforesaid ingredients.

In the latter case, the other ingredients usable are not specifically restricted, and examples thereof include those ingredients that can be added to coating agents, for example, coating agents for coating of medical instruments (e.g., injection needles, catheters, cannulas). Examples include condensation reaction catalysts, antioxidants, coloring matters, surfactants, slip agents, and priming agents. The content of the other ingredients is not particularly limited so long as the effects of the condensate (1), the polydiorganosiloxane (2) and the amino-group-containing polyorganosiloxane (3) are not spoiled, and can be approximately 0.1 to 5 mass % based on the total amount of the condensate (1), the polydiorganosiloxane (2) and the amino-group-containing polyorganosiloxane (3).

In addition, the coating agent may contain an organic solvent. For example, the organic solvent is not specifically restricted, and the same or similar solvents to those that can be used in coating agents can be used. Examples of the organic solvent include flon solvents such as 1,1,2-trichloro-1,2,2-trifluoroethane, etc., chlorine-containing hydrocarbons such as methylene chloride (dichloromethane), chloroform, etc., aliphatic hydrocarbons such as butane, pentane, hexane, etc., aromatic hydrocarbons such as benzene, toluene, xylene, etc., esters such as ethyl acetate, butyl acetate, etc., water-insoluble ketones such as methyl isobutyl ketone, etc., ethers such as tetrahydrofuran (THF), butyl ether, dioxane, etc., aliphatic alcohols such as methanol, ethanol, isopropanol, etc., volatile siloxanes such as hexamethyldisiloxane, octamethylcyclotetrasiloxane, etc., acetonitrile, dimethyl formamide (DMF), dimethyl sulfoxide (DMSO), and carbon disulfide. These organic solvents may be used either singly or as a mixed solvent obtained by combining two or more of these solvents.

The amount of the organic solvent to be used is not particularly limited. From the viewpoint of ease of coating and the like factors, the amount of the organic solvent can be such that the total concentration of the condensate (1), the polydiorganosiloxane (2) and the amino-group-containing polyorganosiloxane (3) is approximately 5 to 80 mass %, for example, 57 to 77 mass %.

For example, in the case where a medical instrument (e.g., a needle) is coated with the coating agent, the coating agent may further be diluted with the aforesaid organic solvent. In this case, the coating agent can be diluted with the organic solvent in such a manner that the total concentration of the condensate (1), the polydiorganosiloxane (2) and the amino-group-containing polyorganosiloxane (3) is 1 to 10 mass %, for example, 3 to 7 mass %.

[Method of Preparing the Coating Agent]

An exemplary method of preparing a coating agent is not specifically restricted, and there can be used a method in which the condensate (1), the polydiorganosiloxane (2) and the amino-group-containing polyorganosiloxane (3), together with the aforesaid other ingredients, if desired, are mixed in the aforesaid composition, and stirring and mixing are conducted. In the aforesaid method, it is exemplary to add an organic solvent. As a result, a medical instrument (e.g., a needle) or the like can be coated with the coating agent. The organic solvent is not particularly limited, and the organic solvents described as the aforesaid other ingredients can be used. Stirring and mixing conditions are not specifically restricted. For example, a stirring and mixing temperature can be 25° C. to 130° C., for example, 40° C. to 90° C. In addition, a stirring and mixing time can be 0.5 to 5 hours, for example, 1 to 3 hours. Under such conditions, the condensate (1), the polydiorganosiloxane (2) and the amino-group-containing polyorganosiloxane (3), together with the aforesaid other ingredients, if desired, can be uniformly mixed without causing undesirable reactions.

[Use of the Coating Agent]

An exemplary coating agent can enhance lubricating property and durability of an object to be coated. Therefore, the coating agent can be suitably used especially in the field of medical instruments (for example, needles, catheters, cannulas) that highly demand the aforesaid characteristics. According to an exemplary aspect, provided is a medical instrument surface treated by a curing treatment of the coating agent. In addition, according to an exemplary aspect, provided is a method of producing a medical instrument that includes subjecting a surface of the medical instrument to a curing treatment with the coating agent.

The medical instrument may be used in any application where the aforesaid characteristics are desired. Examples of the applicable use include catheters, cannulas, needles, three-way cocks, and guide wires. Among these, the coating agent can be used for catheters, cannulas, needles and three-way cocks, for example, for needles, for example, medical needles (for example, injection needles). In an exemplary embodiment, there is provided a needle surface treated by a curing treatment of an exemplary coating agent. According to the coating agent, friction at the time of puncture is reduced, and, durability of the coating is excellent. From the viewpoint of these characteristics, therefore, the needle, for example, the medical needle (for example, injection needle), is more exemplary as the puncture resistance (maximum resistance value) after puncturing a rubber stopper by the needle ten times is smaller. For example, it is exemplary that the aforesaid puncture resistance (maximum resistance value) is less than 50 mN, for example, not more than 45 mN. For example, as for the lower limit for the puncture resistance (maximum resistance value) after puncturing a rubber stopper by the needle ten times, a lower value can be more preferable; therefore, the lower limit is not particularly restricted, and 0 mN, but, normally, a value of not less than 10 mN is allowable. The puncture resistance (maximum resistance value) can be measured by the method described in Examples.

In addition, provided is a method of producing a needle (medical needle) that includes subjecting a surface of a needle (medical needle) to a curing treatment with an exemplary coating agent.

The medical instrument (as a substrate) may be formed of any material, and the same or similar materials to conventional ones can be used. While the following description will be made by taking as an example an embodiment in which the medical instrument is a needle, the present disclosure is not limited to the following embodiment, and the present disclosure is applicable, for example, by using a material constituting a desired medical instrument in place of a material constituting a needle.

The needle may be formed of any material, and there can be used the same or similar materials to those usually used for needles, particularly medical needles (for example, injection needles), such as metallic materials and polymeric materials.

Examples of the metallic materials include, but are not limited to, various stainless steels (SUS) such as SUS304, SUS316L, SUS420J2, SUS630, etc., gold, platinum, silver, copper, nickel, cobalt, titanium, iron, aluminum, tin, various alloys such as nickel-titanium (Ni—Ti) alloys, nickel-cobalt (Ni—Co) alloys, cobalt-chromium (Co—Cr) alloys, zinc-tungsten (Zn—W) alloys, etc., and, further, metal-ceramic composite materials. The aforesaid metallic materials may be used either singly or in combination of two or more of them.

For example, the aforesaid metallic materials ensure that hydroxyl groups on the substrate surface are bound with the —NR— and hydroxyl groups of the condensate (1) constituting the coating agent or the amino groups of the amino-group-containing polyorganosiloxane (3) constituting the coating agent. Therefore, the needles formed of the aforesaid materials are excellent in adhesion to the coating film formed by use of the coating agent of the an exemplary aspect.

Examples of the polymeric materials include, but are not limited to, polyamide resins such as nylon 6, nylon 11, nylon 12, nylon 66 (all registered trademarks), etc., polyolefin resins such as polyethylene resins including linear low-density polyethylene (LLDPE), low-density polyethylene (LDPE) and high-density polyethylene (HDPE), polypropylene resins, etc., modified polyolefin resins, epoxy resins, urethane resins, diallyl phthalate resins (allyl resins), polycarbonate resins, fluoro-resins, amino resins (urea resins, melamine resins, benzoguanamine resins), polyester resins, styrene resins, acrylic resins, polyacetal resins, vinyl acetate resins, phenolic resins, vinyl chloride resins, silicone resins (silicon resins), polyether resins, and polyimide resins. The polymeric materials may be used either singly or in combination of two or more of them.

In addition, the substrate to be surface treated with the coating agent according to an exemplary aspect can be a substrate having a functional group such as a hydroxyl group, a carboxyl group and an amino group, from the viewpoint of easy interaction with the functional groups such as amino group and hydroxyl group possessed by the coating agent according to an exemplary aspect. For example, in the case where the substrate is a metallic material, the metallic material is coated on its surface with an oxide film and has hydroxyl groups or the like, so that the metallic material is high in adhesion to the coating agent. In the case of a substrate having little interaction with the functional groups such as amino group and hydroxyl group possessed by the coating agent according to an exemplary aspect, functional groups such as hydroxyl group may be imparted to the substrate by a plasma treatment or the like, whereby adhesion between the coating agent and the substrate can be enhanced.

While the method for surface treatment with the coating agent according to an exemplary aspect is not specifically restricted, it is exemplary that a curing treatment is conducted by heating, or irradiating with radiation, a coating film that contains the coating agent. For example, provided is a method of producing a medical instrument (for example, a needle), the method including forming a coating film containing the coating agent according to an exemplary aspect on a surface of a medical instrument (for example, a needle) and performing a curing treatment by heating, or irradiating with radiation, the coating film. The surface treatment method by the coating agent according to an exemplary aspect can include performing a curing treatment by heating and humidifying a coating film that contains the coating agent. For example, provided is a method of producing a medical instrument (for example, a needle), the method including forming a coating film containing the coating agent on a surface of a medical instrument (for example, a needle) and performing a curing treatment by heating and humidifying the coating film.

The method of forming the coating film containing the coating agent is not specifically restricted, and any suitable application methods can be applied. For example, as a technique of performing coating, there can be applied an immersion method (dipping method), an applying or printing method, a spraying method, a brushing method, a spin coating method, a coating agent-impregnated sponge coating method and the like. In the case of coating a needle surface with the coating agent, a gas such as air may be fed into the inside of the needle to, for example, prevent the coating agent from entering into the inside of the needle. For example, by this, clogging of the needle with the coating agent can be prevented from occurring. In addition, the coating agent with which a substrate is coated may be subjected to volatilization of solvent by air-drying or heating or the like, if desired, or may in some cases be subjected to precuring of the coating agent simultaneously.

For example, in the case of forming a coating film on only part of the needle surface, only part of the needle surface may be immersed in the coating agent to coat part of the needle surface with the coating agent (coating solution), thereby forming a coating film on a desired surface part of the needle surface. For example, in the case where it is difficult to immerse only part of the needle surface in the coating agent, a process may be adopted in which a needle surface part not needing formation of a coating film thereon is preliminarily protected (e.g., covered) with an appropriate member or material that is attachable and detachable, then the needle is immersed in the coating agent to coat the needle surface with the coating agent, and the protective member (material) on the needle surface part not needing the formation of a coating film is detached, whereby a coating film can be formed on only a desired surface part of the needle surface. The present disclosure is not limited in any way to these formation methods, and a coating film can be formed by appropriately utilizing any suitable methods. For instance, in the case where it is difficult to immerse only part of a needle surface in the coating agent, other coating method (for example, application method, spraying method, etc.) than the immersion method may be applied in place of the immersion method. In the case where both the outer surface and the inner surface of the needle surface should have a lubricating property and durability, an immersion method (dipping method) can be used, in view of that both the outer surface and the inner surface can thereby be coated at a time.

For example, after the coating film containing the coating agent is formed as described above, a curing treatment of the coating film can be conducted.

In regard of the curing treatment (surface treatment), the method for the curing treatment (surface treatment) in the case of heating the coating film containing the coating agent is not specifically restricted. Examples of the curing treatment (surface treatment) include a heating treatment under normal pressure (atmospheric pressure), a heating treatment under compressed steam, and a heating treatment using ethylene oxide gas (EOG).

Heating treatment conditions (reaction conditions) in the case of the heating treatment under normal pressure (atmospheric pressure) are not particularly limited, so long as they are conditions under which a desired effect (for example, lubricating property, durability) can be achieved. The heating temperature can be 50° C. to 150° C., for example, 60° C. to 130° C. In addition, the heating time can be 2 to 48 hours, for example, 15 to 30 hours. Under such reaction conditions, for example, the condensate (1) (—NR— and hydroxyl group) and the amino-group-containing polyorganosiloxane (3) (amino group) can firmly bind to a substrate. For example, the condensate (1) (—NR— and hydroxyl group) reacts with the substrate surface, whereby a firm coating film can be formed. In addition, as the heating means (device), there can be utilized, for example, an oven, a dryer, a microwave heater and the like.

Heating treatment conditions (reaction conditions) in the case of the heating treatment under compressed steam are also not particularly limited, so long as they are conditions under which a desired effect (for example, lubricating property, durability) can be achieved. The hearing temperature can be 100° C. to 135° C., for example, 105° C. to 130° C. In addition, the heating time can be 1 to 60 minutes, for example, 10 to 30 minutes. Further, the pressure may be appropriately selected, taking a desired reactivity (for example, lubricating property, durability, binding property for binding to a substrate) and the like into consideration. Under such reaction conditions, the condensate (1) (—NR— and hydroxyl group) and the amino-group-containing polyorganosiloxane (3) (amino group) can firmly bind to a substrate. The condensate (1) (—NR— and hydroxyl group) reacts with the substrate surface, whereby a firm coating film can be formed. In addition, under the aforesaid conditions, a needle can be simultaneously subjected to a sterilization treatment. As the heating means (device), there can be utilized, for example, a Koch's sterilizer, an autoclave and the like.

Heating treatment conditions (reaction conditions) in the case of the heating treatment using ethylene oxide gas (EOG) are also not particularly limited, so long as they are conditions under which a desired effect (for example, lubricating property, durability) can be achieved. The heating temperature can be 40° C. to 135° C., for example, 45° C. to 80° C. In addition, the heating time can be 1 to 300 minutes, for example, 20 to 250 minutes. Further, the pressure may be appropriately selected, taking a desired reactivity (for example, lubricating property, durability, binding property for binding to a substrate) and the like into consideration. Under such reaction conditions, the condensate (1) (—NR— and hydroxyl group) and the amino-group-containing polyorganosiloxane (3) (amino group) can firmly bind to a substrate. For example, the condensate (1) (—NR— and hydroxyl group) reacts with the substrate surface, whereby a firm coating film can be formed. In addition, under the aforesaid conditions, a needle can simultaneously be subjected to a sterilization treatment.

The radiation in the case of performing the curing treatment (surface treatment) by irradiation with radiation is not specifically restricted, and can be gamma rays (γ rays), electron beams, neutron beams, or X rays. Among these, exemplary are gamma rays and electron beams. By irradiating with radiation, it is possible not only to accelerate the curing treatment of the coating agent but also to sterilize the needle. Radiation irradiation conditions (reaction conditions) are not specifically restricted, so long as they are conditions under which a desired effect (for example, lubricating property, durability) can be achieved. For instance, in the case of irradiation with gamma rays, the conditions such as dose and irradiation time are not particularly limited. For example, γ ray dose is 10 to 50 kGy, for example, 15 to 25 kGy. Under such irradiation conditions, the condensate (1) (—NR— and hydroxyl group) and the amino-group-containing polyorganosiloxane (3) (amino group) can firmly bind to a substrate. In addition, the condensate (1) (—NR— and hydroxyl group) reacts with the substrate surface, whereby a firm coating film can be formed.

EXAMPLES

Exemplary effects of the present disclosure will be described below, using the following Examples and Comparative Examples. It is to be noted, however, that the technical scope of the present invention is not to be limited only to the following Examples. Note that in the following Examples, the operations were carried out at room temperature (25° C.), unless specified otherwise. In addition, "%" and "parts" mean "mass %" and "parts by mass," respectively, unless otherwise specified.

Synthesis Example 1: Synthesis of Condensate (1)

A condensate (1) was synthesized in the following manner. 100 parts by mass of a both terminal silanol group-containing polydimethylsiloxane (weight average molecular weight=approximately 900,000; in the general formula (1-1), m=12,000) of the following structure, 5 parts by mass of a compound (A) of the following structure, and 1090 parts by mass of dehydrated toluene were added, and the admixture was stirred at 85° C. for eight hours. After reaction was allowed for a predetermined time, the reaction liquid was purified by a gel filtration column, to synthesize the condensate (1). Note that the following compound (A) was obtained by a condensation reaction between γ-aminopropyltrimethoxysilane and γ-glycidoxypropyltrimethoxysilane.

[Chemical 26]
Both terminal silanol group-containing polydimethylsiloxane (corresponding to compound (1-1))

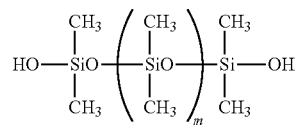

In the aforesaid structure, m=12,000

Compound (A) (corresponding to compound (1-2))

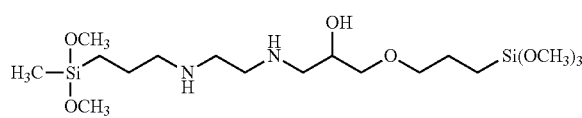

Synthesis Example 2: Synthesis of Both Terminal Amino Group-Containing Polyorganosiloxane (4)

A both terminal amino group-containing polyorganosiloxane (4) of the following structure was synthesized in the same manner as in Preparation Example 1 of Japanese Patent Laid-open No. 1995-178159, in the following way.

[Chemical 27]
Both terminal amino group-containing polyorganosiloxane (4)

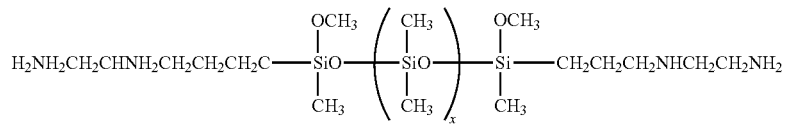

In the aforesaid structure, x=12,000

390 parts by mass of toluene was added to 100 parts by mass of a both terminal silanol group-containing polydimethylsiloxane (weight average molecular weight=approximately 900,000) of the following structure, the resulting admixture was stirred for three hours at 50° C., then 20 parts by mass of γ-[N-(β-aminoethyl)amino]propylmethyldimethoxysilane was added thereto, and reaction was allowed at 80° C. for 12 hours, to obtain the both terminal amino group-containing polyorganosiloxane (4) (weight average molecular weight=approximately 900,000). Note that the both terminal amino group-containing polyorganosiloxane (4) will sometimes be referred to as "compound (4)."

[Chemical 28]
Both terminal silanol group-containing polydimethylsiloxane (corresponding to compound (1-1))

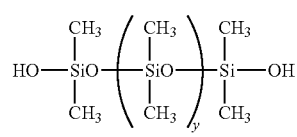

In the aforesaid structure, y=12,000

Synthesis Example 3: Synthesis of Condensate (1')

A condensate (1') was prepared in the same manner as in Synthesis Example 1, except that the kind of the both terminal silanol group-containing polydimethylsiloxane in Synthesis Example 1 was changed to a compound (weight average molecular weight=approximately 22,000; m=300) represented by the following structural formula.

[Chemical 29]
Both terminal silanol group-containing polydimethylsiloxane

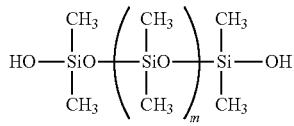

In the aforesaid structure, m=300

Comparative Example 1

120 parts by mass of the both terminal amino group-containing polyorganosiloxane (4) synthesized in Synthesis Example 2, 730 parts by mass of a polydimethylsiloxane (2) (weight average molecular weight=approximately 3,200; in the general formula (2), n=approximately 40) of the following structure, 660 parts by mass of an amino-group-containing polyorganosiloxane (3) (weight average molecular weight=approximately 15,000) of the following structure, 1,700 parts by mass of toluene, and 200 parts by mass of ethanol were added, and the resulting admixture was stirred at 85° C. for two hours, to obtain a comparative coating agent 1.

[Chemical 30]
Polydimethylsiloxane (2)

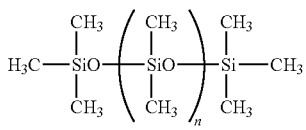

Amino-Group-Containing Polyorganosiloxane (3)

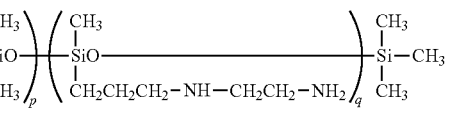

where q=5, q:p (molar ratio)=1:40

Example 1

105 parts by mass of the condensate (1) (weight average molecular weight=approximately 900,000) synthesized in Synthesis Example 1, 730 parts by mass of a polydimethylsiloxane (2) (weight average molecular weight=approximately 3,200; in the general formula (2), n=approximately 40) of the following structure, 990 parts by mass of an amino-group-containing polyorganosiloxane (3) (weight average molecular weight=approximately 15,000) of the following formula, 1,200 parts by mass of toluene, and 100 parts by mass of ethanol were added, and the resulting admixture was stirred at 85° C. for two hours, to obtain a coating agent 1.

[Chemical 31]
Polydimethylsiloxane (2)

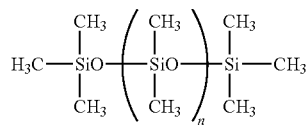

Amino-Group-Containing Polyorganosiloxane (3)

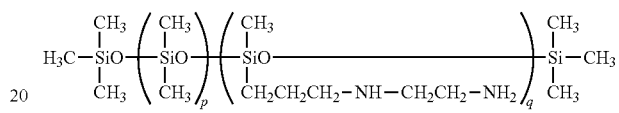

where q=5, q:p (molar ratio)=1:40

Examples 2 to 4 and Comparative Examples 2 and 3

Coating agents 2 to 4 (Examples 2 to 4) and comparative coating agents 2 and 3 (Comparative Examples 2 and 3) were obtained in the same manner as in Example 1 above, except that the condensate (1) synthesized in Synthesis Example 1, the polydimethylsiloxane (2) of the aforesaid structure, the amino-group-containing polyorganosiloxane (3) of the aforesaid structure, toluene and ethanol were changed in such a manner as to obtain the compositions set forth in Table 1 below.

Example 5

A coating agent 5 (Example 5) was obtained in the same manner as in Example 2 above, except that the kind of the polydimethylsiloxane (2) used in Examples 2 was changed to a polydimethylsiloxane (2) (weight average molecular weight=6,600; n in the general formula (2)=approximately 90) of the following structural formula.

[Chemical 32]
Polydimethylsiloxane (2)

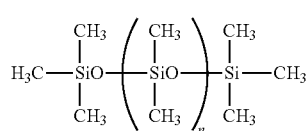

Comparative Example 4

A comparative coating agent 4 (Comparative Example 4) was obtained in the same manner as in Example 2 above, except that the kind of the condensate (1) used in Example 2 was changed to the condensate (1') synthesized in Synthesis Example 3.

Note that in Table 1 below, the condensate (1) synthesized in Synthesis Example 1 above is referred to as "condensate (1)," the polydimethylsiloxane (2) is referred to as "compound (2)," and the amino-group-containing polyorganosiloxane (3) is referred to as "compound (3)." Note that in Comparative Example 1, γ-[N-(β-aminoethyl)amino]propylmethyldimethoxysilane is not a compound (1-2) and, therefore, the compound (4) does not correspond to the condensate (1). However, for comparison, in Table 1, the condensate obtained using γ-[N-(β-aminoethyl)amino]propylmethyldimethoxysilane is described as a substance corresponding to the condensate (1), in place of the compound (1-2). In addition, in Table 1, the "total amount of silane compounds" means the total mass of the condensate (1), the compound (2) and the compound (3).

injection needles 1 to 5, whereas the injection needles formed on surfaces thereof with coating films using the comparative coating agents 1 to 4 are referred to as comparative injection needles 1 to 4, respectively.

(Injection Needle Coating 2: EOG)

Coating Liquids were Prepared in the Same Manner as the Aforesaid (Injection Needle Coating 1: Heating).

In each of the coating liquids prepared as aforesaid, an 18G injection needle (with a needle part made of SUS304) was immersed, and the injection needle was pulled up at a rate of 1,000 mm/minute, by use of a tensile tester (Auto-

TABLE 1

|  |  | Com 1 | Com 2 | Ex 1 | Ex 2 | Ex 3 | Ex 4 | Com 3 | Ex 5 | Com 4 |
|---|---|---|---|---|---|---|---|---|---|---|
| Blending ratio (parts by mass) | Condensate (1) | (120)*[1] | 105 | 105 | 105 | 105 | 105 | 105 | 105 | 105 |
|  | m in Compound (1-1) | (1,200)*[1] | 12,000 | 12,000 | 12,000 | 12,000 | 12,000 | 12,000 | 12,000 | 300 |
|  | Compound (2)*[2] | 730 | 365 | 730 | 1,500 | 2,000 | 3,000 | 4,000 | 1,500 | 1,500 |
|  | n in Compound (2) | 40 | 40 | 40 | 40 | 40 | 40 | 40 | 90 | 40 |
|  | Compound 3*[3] | 660 | 800 | 990 | 990 | 990 | 990 | 990 | 990 | 990 |
|  | Total amount of silane compound | 1,510 | 1,270 | 1,825 | 2,595 | 3,095 | 4,095 | 5,095 | 2,595 | 2,595 |
|  | Toluene | 1,700 | 1,200 | 1,200 | 1,200 | 1,200 | 1,200 | 1,200 | 1,200 | 1,200 |
|  | Ethanol | 200 | 100 | 100 | 100 | 100 | 100 | 100 | 100 | 100 |
|  | Total amount | 3,410 | 2,570 | 3,125 | 3,895 | 4,395 | 5,395 | 6,395 | 3,895 | 3,895 |
| Content ratio (mass %) | Condensate (1) | 7.9% | 8.3% | 5.8% | 4.0% | 3.4% | 2.5% | 2.1% | 4.0% | 4.0% |
|  | Compound (2)*[2] | 48.3% | 28.7% | 40.0% | 57.8% | 64.6% | 73.3% | 78.5% | 57.8% | 57.8% |
|  | Compound (3)*[3] | 43.8% | 63.0% | 54.2% | 38.2% | 32.0% | 24.2% | 19.4% | 38.2% | 38.2% |

*[1]These indicate the mass of the condensate using γ-[N-(β-aminoethyl)amino]propylmethyldimethoxysilane and the polymerization degree of the compound (1-1) used for synthesis of the condensate, respectively.
*[2]Compound (2): polydimethylsiloxane (2)
*[3]Compound (3): amino-group-containing polyorganosiloxane (3)
Com: Comparative Example
Ex: Example For the coating agents 1 to 5 obtained in Examples 1 to 5 above and the comparative coating agents 1 to 4 obtained in Comparative Examples 1 to 4, piercing resistance was measured according to the following method.

[Measurement of Piercing Resistance]

(Injection Needle Coating 1: Heating)

Each coating agent was diluted by addition of dichloromethane in such a manner that the concentration of silicone components became approximately 5 mass %, to obtain a colorless transparent coating liquid. Note that the concentration of the silicone components, in Examples 1 to 4 and Comparative Examples 2 and 3, refers to the total concentration of the condensate (1), the polydimethylsiloxane (2) and the amino-group-containing polyorganosiloxane (3) in the coating liquid. In Comparative Example 1, the concentration of the silicone components refers to the total concentration of the both terminal amino group-containing polyorganosiloxane (4), the polydimethylsiloxane (2) and the amino-group-containing polyorganosiloxane (3) in the coating liquid.

In each of the coating liquids prepared as aforesaid, an 18G injection needle (with a needle part made of SUS304) was immersed, and the injection needle was pulled up at a rate of 1,000 mm/minute, by use of a tensile tester (Autograph AG-1kNIS, made by Shimadzu Corporation). Natural drying at room temperature was conducted for two hours. Further, the injection needle was heated in an oven at 105° C. for 24 hours, to perform a curing treatment. Note that the injection needles formed on surfaces thereof with coating films using the coating agents 1 to 5 are referred to as graph AG-1kNIS, made by Shimadzu Corporation). Natural drying at room temperature was conducted for two hours. Further, the injection needle was subjected to a curing treatment using ethylene oxide gas (EOG) at 50° C. for 210 minutes. Note that by the aforesaid treatment, the injection needle underwent EOG (ethylene oxide gas) sterilization. The injection needles formed on surfaces thereof with coating films using the coating agents 1 to 4 are referred to as injection needles 6 to 9, whereas the injection needles formed on surfaces thereof with coating films using the comparative coating agents 1 to 3 are referred to as comparative injection needles 5 to 7, respectively.

(Injection Needle Coating 3: High-Pressure Steam)

Coating Liquids were Prepared in the Same Manner as in the Aforesaid (Injection Needle Coating 1: Heating).

In each of the coating liquids prepared as aforesaid, an 18G injection needle (with a needle part made of SUS304) was immersed, and the injection needle was pulled up at a rate of 1,000 mm/minute, by use of a tensile tester (Autograph AG-1kNIS, made by Shimadzu Corporation). Natural drying at room temperature was conducted for two hours. Further, the injection needle was subjected to a curing treatment under a high-pressure steam at 121° C. for 20 minutes. Note that by the aforesaid treatment, the injection needle underwent high-pressure steam (autoclave) sterilization. The injection needles formed on surfaces thereof with coating films using the coating agents 1 to 4 are referred to as injection needles 10 to 13, whereas the injection needles formed on surfaces thereof with coating films using the comparative coating agents 1 to 3 are referred to as comparative injection needles 8 to 10, respectively.

(Injection Needle Coating 4: Radiation)

Coating Liquids were Prepared in the Same Manner as the Aforesaid (Injection Needle Coating 1: Heating).

In each of the coating liquids prepared as aforesaid, an 18G injection needle (with a needle part made of SUS304) was immersed, and the injection needle was pulled up at a rate of 1,000 mm/minute, by use of a tensile tester (Autograph AG-1kNIS, made by Shimadzu Corporation). Natural drying at room temperature was conducted for two hours. Further, the injection needle was subjected to a curing treatment by irradiating with γ rays at 20 kGy. Note that by the aforesaid treatment, the injection needle underwent radiation sterilization. The injection needles formed on surfaces thereof with coating films using the coating agents 1 to 4 are referred to as injection needles 14 to 17, whereas the injection needles formed on surfaces thereof with coating films using the comparative coating agents 1 to 3 are referred to as comparative injection needles 11 to 13, respectively.

(Measurement of Piercing Resistance)

For the injection needles 1 to 17 and the comparative injection needles 1 to 13, sliding resistance value (piercing resistance value) (mN) at the time of puncturing a 50 μm-thick polyethylene film with the injection needle at an angle of 90 degrees and at a rate of 100 mm/minute was measured, using a tensile tester (Autograph AG-1kNIS, made by Shimadzu Corporation). Specifically, sliding resistance in relation to moving amount of the injection needle was obtained as time-series data. In addition, from the measurements, a maximum resistance value (mN) was calculated. Note that the measurement was conducted after the injection needles 1 to 17 and the comparative injection needles 1 to 13 were each made to puncture a rubber stopper zero time (initial stage) and ten times.

Figure 1B:
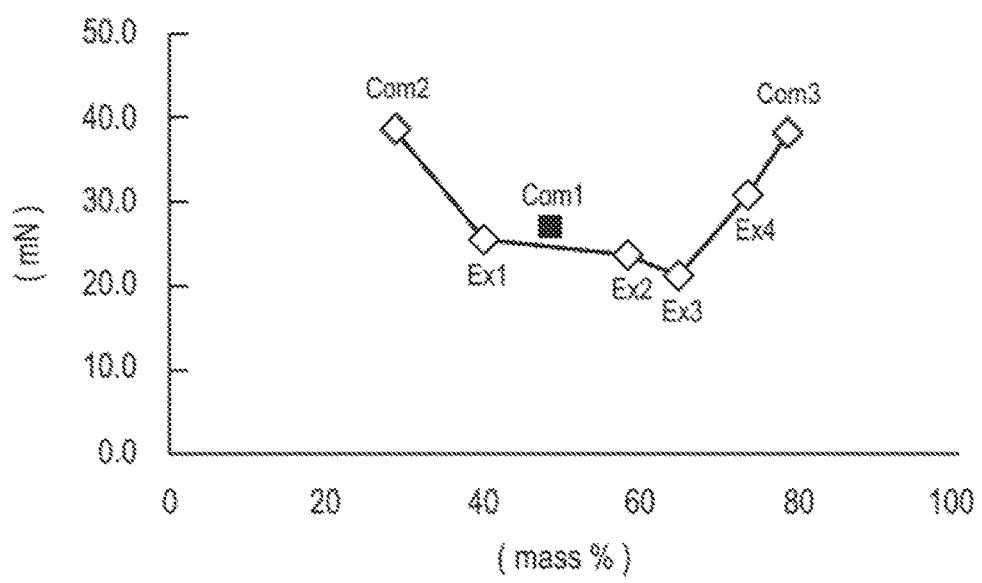
FIG. 1B is a graph depicting puncture resistance (sliding resistance value (mN)) at an initial stage (on puncturing zero time) of a needle surface treated with a coating agent by an EOG treatment, in Examples 1 to 4 (Ex. 1 to Ex. 4) and Comparative Examples 1 to 3 (Com. 1 to Com. 3).
Figure 1C:
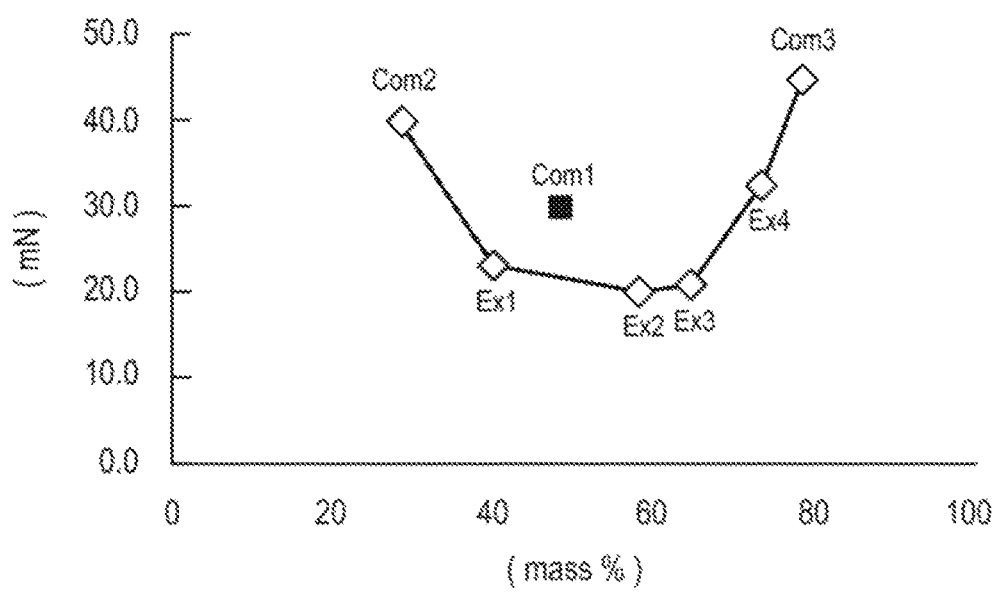
FIG. 1C is a graph depicting puncture resistance (sliding resistance value (mN)) at an initial stage (on puncturing zero time) of a needle surface treated with a coating agent by a high-pressure steam treatment, in Examples 1 to 4 (Ex. 1 to Ex. 4) and Comparative Examples 1 to 3 (Com. 1 to Com. 3).
Figure 2A:
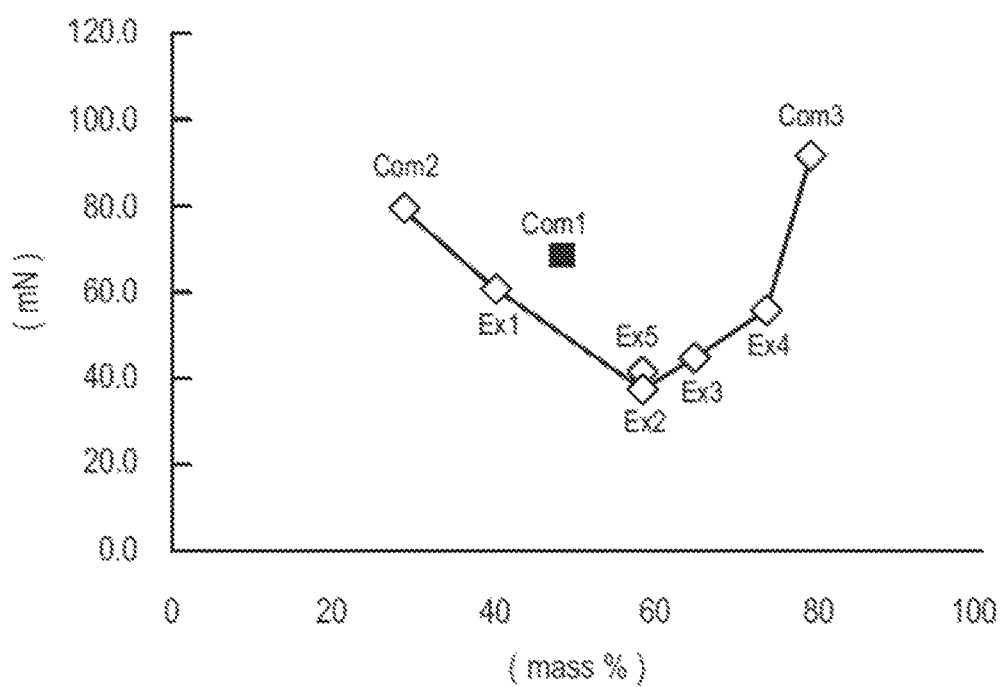
FIG. 2A is a graph depicting puncture resistance (sliding resistance value (mN)), on puncturing ten times, of a needle surface treated with a coating agent by heating, in Examples 1 to 5 (Ex. 1 to Ex. 5) and Comparative Examples 1 to 3 (Com. 1 to Com. 3).
Figure 2B:
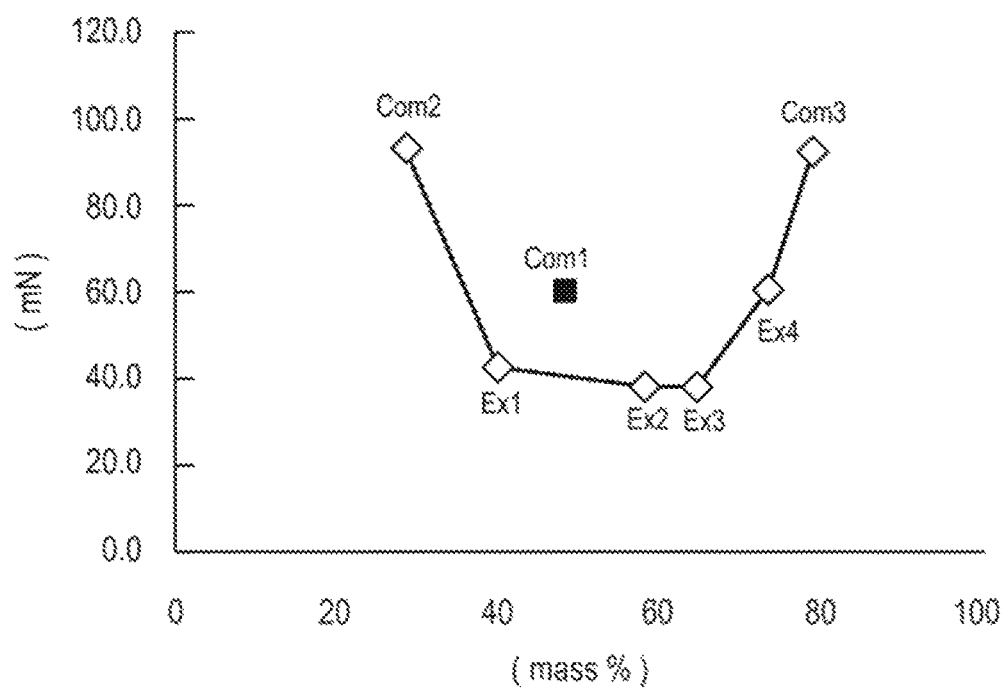
FIG. 2B is a graph depicting puncture resistance (sliding resistance value (mN)), on puncturing ten times, of a needle surface treated with a coating agent by an EOG treatment, in Examples 1 to 4 (Ex. 1 to Ex. 4) and Comparative Examples 1 to 3 (Com. 1 to Com. 3).
Figure 2C:
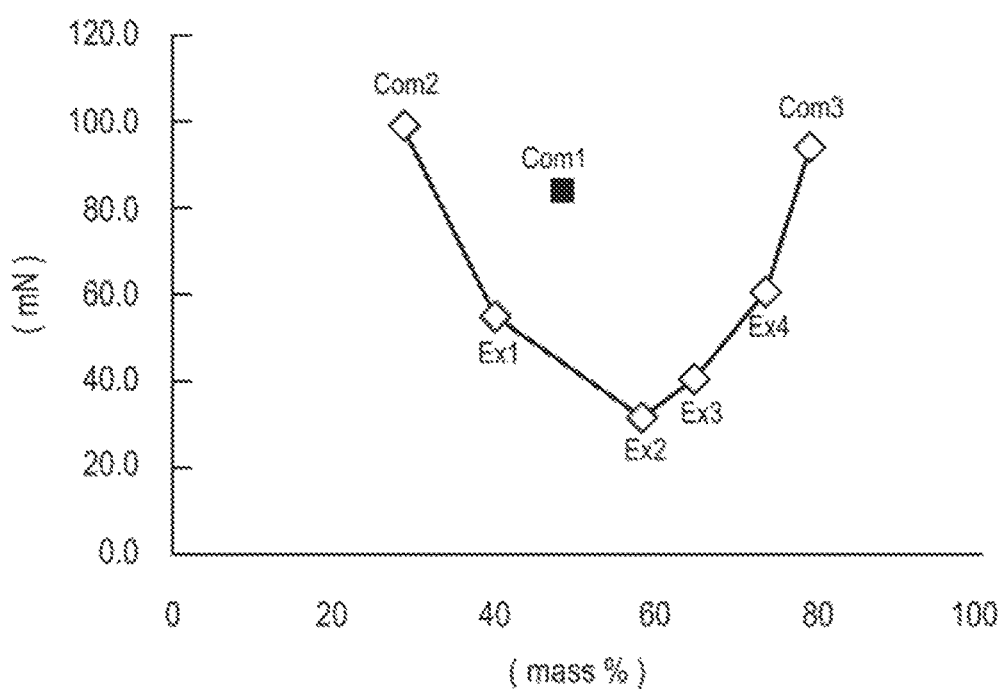
FIG. 2C is a graph depicting puncture resistance (sliding resistance value (mN)), on puncturing ten times, of a needle surface treated with a coating agent by a high-pressure steam treatment, in Examples 1 to 4 (Ex. 1 to Ex. 4) and Comparative Examples 1 to 3 (Com. 1 to Com. 3).

The results are depicted in FIGS. 1 and 2. Note that in FIGS. 1 and 2, the axis of ordinates represents sliding resistance value (unit: mN). The axis of abscissas represents the content ratio (unit:mass %) of the compound (2), based on the total mass of the compound (1), the compound (2) and the compound (3). In detail, the results of sliding resistance value (piercing resistance value) (mN) upon puncturing zero time and upon puncturing ten times, for the injection needles 1 to 5 and the comparative injection needles 1 to 4 (coating 1:heating at 105° C. for 24 hours), are depicted in FIG. 1A and FIG. 2A, respectively. In addition, the results of sliding resistance value (piercing resistance value) (mN) upon puncturing zero time and upon puncturing ten times, for the injection needles 6 to 9 and the comparative injection needles 5 to 7 (coating 2: EOG treatment), are depicted in FIG. 1B and FIG. 2B, respectively. The results of sliding resistance value (piercing resistance value) (mN) upon puncturing zero time and upon puncturing ten times, for the injection needles 10 to 13 and the comparative injection needles 8 to 10 (coating 3: high-pressure steam treatment), are depicted in FIG. 1C and FIG. 2C, respectively. Note that the plots in the polygonal lines in FIGS. 1 and 2 represent Comparative Example 2 (Com 2), Example 1 (Ex 1), Example 2 (Ex 2), Example 3 (Ex 3), Example 4 (Ex 4) and Comparative Example 3 (Com 3), from the left. In FIG. 1A, Example 5 (Ex 5) and Comparative Example 4 (Com 4) are depicted in addition to the aforesaid, and, in FIG. 2A, Example 5 (Ex 5) is depicted in addition to the aforesaid. "Com 1" in FIGS. 1 and 2 represents Comparative Example 1.

From FIGS. 1 and 2, the injection needles according to an exemplary aspect exhibited some sliding resistance values (piercing resistance values) comparable to those of the comparative injection needles upon puncturing zero times, but exhibited sliding resistance values (piercing resistance values) significantly lower than those of the comparative injection needles upon puncturing ten times. Therefore, it is considered that according to the injection needles according to an exemplary aspect, durability can be enhanced. Note that while the results in regard of coating 4 (γ ray irradiation) are not illustrated, sliding resistance values (piercing resistance values) (mN) after puncturing a rubber stopper with the injection needles 15 and 16 ten times exhibited sliding resistance values (piercing resistance values) significantly lower than those of the comparative injection needles 11 to 13. Therefore, it is considered that the injection needles according to an exemplary aspect can hold excellent piercing characteristics and are excellent in durability. In addition, from the aforesaid results, it is expected that the coating agent according to an exemplary aspect can exhibit the same or similar lubricating property and durability to the aforesaid, also when applied to other medical instruments than needles.

What is claimed is:

1. A coating agent, comprising:
   (a) a condensate of a compound represented by the following general formula (1-1):

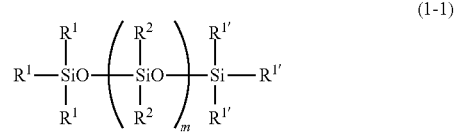

(1-1)

wherein each $R^1$ and each $R^{1'}$ independently represents a monovalent hydrocarbon group or a hydroxyl group (—OH), provided that at least one of $R^1$ and at least one of $R^{1'}$ is the hydroxyl group (—OH), each $R^2$ independently represents a monovalent hydrocarbon group, and m is an integer of 1,000 to 30,000, with a compound represented by the following general formula (1-2):

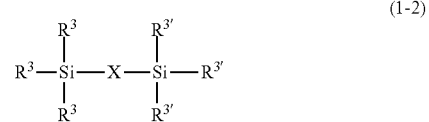

(1-2)

wherein each $R^3$ and each $R^{3'}$ independently represents a $C_1$-$C_4$ monovalent hydrocarbon group or a $C_1$-$C_4$ alkoxy group, provided that at least one of $R^3$ and at least one of $R^{3'}$ is the $C_1$-$C_4$ alkoxy group, X is a divalent group having at least one —NR—, wherein each R is independently a hydrogen atom or a monovalent hydrocarbon group, and at least one hydroxyl group (—OH);

(b) a polydiorganosiloxane represented by the following general formula (2):

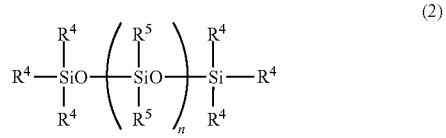

(2)

wherein each $R^4$ and $R^5$ independently represents a monovalent hydrocarbon group, and
n is an integer of 8 to 1,000; and
(c) an amino-group-containing polyorganosiloxane containing at least one amino group in one molecule thereof represented by the following general formula (3):

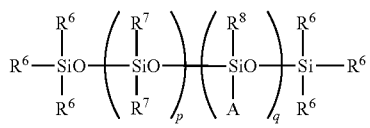

(3)

wherein each $R^6$ independently represents a monovalent hydrocarbon group or a —$OR^9$ group, wherein each $R^9$ independently represents a substituted or unsubstituted $C_1$-$C_4$ monovalent hydrocarbon group,
each $R^7$ and each $R^8$ independently represents a monovalent hydrocarbon group,
each A independently represents an amino-group-containing group,
a ratio of p:q is in a range of from 5:1 to 100:1, and
q is an integer of 1 to 100,
wherein the content ratio of the polydiorganosiloxane is 30 to 75 mass %, based on the total mass of the condensate, the polydiorganosiloxane and the amino-group-containing polyorganosiloxane.

2. The coating agent according to claim 1, wherein in the general formula (1-2), X is represented by the general formula (i):

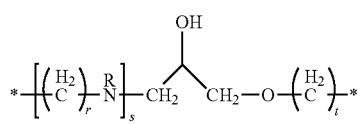

(i)

wherein R is each independently a hydrogen atom or a monovalent hydrocarbon group,
r, s and t are each independently an integer of 1 to 6, and
* represents a binding position.

3. The coating agent according to claim 2, wherein in the general formula (i), R is a hydrogen atom or a $C_1$-$C_4$ straight-chain or branched alkyl group, r is an integer of 2 to 3, s is an integer of 2 to 3, and t is an integer of 2 to 3.

4. The coating agent according to claim 1, wherein in the general formula (1-2), all of $R^3$ groups or all of $R^{3'}$ groups are alkoxy groups.

5. The coating agent according to claim 1, wherein in the general formula (3), the amino-group-containing group is γ-aminopropyl group, N-(β-aminoethyl)aminomethyl group or γ-(N-(β-aminoethyl)amino)propyl group.

6. The coating agent according to claim 1, wherein the amount of the condensate is 2.3 to 8.0 mass %, based on the total mass of the condensate, the polydiorganosiloxane and the amino-group-containing polyorganosiloxane.

7. The coating agent according to claim 1, wherein the amount of the amino-group-containing polyorganosiloxane is 20 to 62 mass %, based on the total mass of the condensate, the polydiorganosiloxane and the amino-group-containing polyorganosiloxane.

8. The coating agent according to claim 1, wherein in the compound represented by the general formula (1-1), one of the $R^1$ groups is the hydroxyl group, one of the $R^{1'}$ groups is the hydroxyl group, and each of the remaining $R^1$ and $R^{1'}$ groups that is not a hydroxyl group independently is a $C_1$-$C_4$ straight-chain or branched alkyl group; and each $R^2$ independently is a $C_1$-$C_4$ straight-chain or branched alkyl group.

9. The coating agent according to claim 1, wherein in the compound represented by the general formula (1-1), one of the $R^1$ groups is the hydroxyl group, one of the $R^{1'}$ groups is the hydroxyl group, and each of the remaining $R^1$ and $R^{1'}$ groups that is not a hydroxyl group is a methyl group; and each $R^2$ is a methyl group.

10. A method for surface treating a medical instrument, the method comprising:
forming a coating film on a surface of a medical instrument, wherein the coating film comprises the coating agent according to claim 1, and
curing the coating film.

11. The method according to claim 10, wherein the step of curing the coating film comprises heating the coating film or irradiating the coating film with radiation.

12. The method according to claim 11, wherein the step of curing the coating film comprises heating the coating film at a temperature of from 50° C. to 150° C. for a duration of from 2 to 48 hours.

13. The method according to claim 11, wherein the step of curing the coating film comprises heating the coating film under compressed steam at a temperature of from 100° C. to 135° C. for a duration of from 1 to 60 minutes.

14. The method according to claim 11, wherein the step of curing the coating film comprises heating the coating film using ethylene oxide gas at a temperature of from 40° C. to 135° C. for a duration of from 1 to 300 minutes.

15. The method according to claim 11, wherein the step of curing the coating film comprises irradiating the coating film with radiation, wherein the radiation comprises gamma rays, electron beams, neutron beams, or X rays.

16. The method according to claim 10, wherein the medical instrument is a needle.

17. A medical instrument obtained from the method according to claim 10.

18. The medical instrument according to claim 17, wherein the medical instrument is a needle.

* * * * *